US010321834B2

(12) United States Patent
Brisben et al.

(10) Patent No.: US 10,321,834 B2
(45) Date of Patent: Jun. 18, 2019

(54) MULTI-VECTOR SENSING IN CARDIAC DEVICES USING A HYBRID APPROACH

(71) Applicant: CARDIAC PACEMAKERS, INC., St. Paul, MN (US)

(72) Inventors: Amy Jean Brisben, St. Paul, MN (US); Venugopal Allavatam, Maple Grove, MN (US); Krzysztof Z. Siejko, Maple Grove, MN (US); Deepa Mahajan, Roseville, MN (US); Kevin G. Wika, Blaine, MN (US); Keith L. Herrmann, Minneapolis, MN (US); Stephen J. Hahn, Shoreview, MN (US)

(73) Assignee: CARDIAC PACEMAKERS, INC., St. Paul, MN (US)

( * ) Notice: Subject to any disclaimer, the term of this patent is extended or adjusted under 35 U.S.C. 154(b) by 147 days.

(21) Appl. No.: 15/297,624

(22) Filed: Oct. 19, 2016

(65) Prior Publication Data

US 2017/0112399 A1    Apr. 27, 2017

Related U.S. Application Data

(60) Provisional application No. 62/245,757, filed on Oct. 23, 2015, provisional application No. 62/245,738, (Continued)

(51) Int. Cl.
*A61B 5/04* (2006.01)
*A61B 5/042* (2006.01)
(Continued)

(52) U.S. Cl.
CPC ........ *A61B 5/04011* (2013.01); *A61B 5/0402* (2013.01); *A61B 5/04012* (2013.01);
(Continued)

(58) Field of Classification Search
CPC .. A61B 5/04011; A61B 5/0402; A61B 5/0452
See application file for complete search history.

(56) References Cited

U.S. PATENT DOCUMENTS

| 5,313,953 A | 5/1994 | Yomtov et al. |
| 5,331,966 A | 7/1994 | Bennett et al. |

(Continued)

FOREIGN PATENT DOCUMENTS

| EP | 1184050 A2 | 3/2002 |
| WO | 2005011809 A2 | 2/2005 |

OTHER PUBLICATIONS

International Search Report and the Written Opinion of the International Searching Authority, or the Declaration, PCT/US2016/057825, dated Jan. 31, 2017.

(Continued)

*Primary Examiner* — Allen Porter
(74) *Attorney, Agent, or Firm* — Seager, Tufte & Wickhem LLP

(57) ABSTRACT

Methods and devices for combining multiple signals from multiple sensing vectors for use in wearable or implantable cardiac devices. A preferred sensing configuration may be selected at a given point in time, for example under clinical conditions. Signal quality for the preferred sensing configuration is then monitored, and if the signal quality degrades under selected conditions, re-analysis may be performed to select a different sensing vector configuration for at least temporary use. If signal quality increases for the preferred sensing configuration, temporary use of the different sensing vector configuration may cease and reversion to the preferred sensing configuration takes place if certain conditions are met. The conditions for reversion may depend in part of a history of sensing signal quality for the preferred sensing configuration.

11 Claims, 16 Drawing Sheets

Related U.S. Application Data filed on Oct. 23, 2015, provisional application No. 62/245,729, filed on Oct. 23, 2015, provisional application No. 62/245,762, filed on Oct. 23, 2015.

(51) Int. Cl.

| | | |
|---|---|---|
| *A61B 5/00* | (2006.01) | |
| *A61N 1/39* | (2006.01) | |
| *A61B 5/0452* | (2006.01) | |
| *A61N 1/362* | (2006.01) | |
| *A61B 5/0402* | (2006.01) | |
| *A61N 1/04* | (2006.01) | |
| *A61N 1/05* | (2006.01) | |
| *A61N 1/365* | (2006.01) | |
| *A61N 1/37* | (2006.01) | |
| *A61B 5/0456* | (2006.01) | |
| *A61B 5/0468* | (2006.01) | |
| *A61B 5/024* | (2006.01) | |
| *A61B 5/0245* | (2006.01) | |
| *A61B 5/0472* | (2006.01) | |

(52) U.S. Cl.
CPC .......... *A61B 5/0422* (2013.01); *A61B 5/0452* (2013.01); *A61B 5/0456* (2013.01); *A61B 5/0468* (2013.01); *A61B 5/686* (2013.01); *A61B 5/72* (2013.01); *A61B 5/7203* (2013.01); *A61B 5/7221* (2013.01); *A61N 1/046* (2013.01); *A61N 1/05* (2013.01); *A61N 1/0563* (2013.01); *A61N 1/3622* (2013.01); *A61N 1/3625* (2013.01); *A61N 1/36514* (2013.01); *A61N 1/3704* (2013.01); *A61N 1/3925* (2013.01); *A61N 1/3956* (2013.01); *A61N 1/3987* (2013.01); *A61B 5/0245* (2013.01); *A61B 5/02416* (2013.01); *A61B 5/042* (2013.01); *A61B 5/04017* (2013.01); *A61B 5/04028* (2013.01); *A61B 5/0472* (2013.01); *A61B 5/04525* (2013.01); *A61B 5/6869* (2013.01)

(56) References Cited

U.S. PATENT DOCUMENTS

| | | | |
|---|---|---|---|
| 5,709,215 | A | 1/1998 | Perttu et al. |
| 6,393,316 | B1 | 5/2002 | Gillberg et al. |
| 6,728,572 | B2 | 4/2004 | Hsu et al. |
| 7,248,921 | B2 | 7/2007 | Palreddy et al. |
| 7,330,757 | B2 | 2/2008 | Ostroff et al. |
| 7,376,458 | B2 | 5/2008 | Palreddy et al. |
| 7,392,085 | B2 | 6/2008 | Warren et al. |
| 7,496,409 | B2 | 2/2009 | Greenhut et al. |
| 7,623,909 | B2 | 11/2009 | Sanghera et al. |
| 7,783,340 | B2 | 8/2010 | Sanghera et al. |
| 8,160,686 | B2 | 4/2012 | Allavatam et al. |
| 8,160,687 | B2 | 4/2012 | Warren et al. |
| 8,185,198 | B2 | 5/2012 | Palreddy et al. |
| 8,200,341 | B2 | 6/2012 | Sanghera et al. |
| 8,457,737 | B2 | 6/2013 | Bardy et al. |
| 8,494,630 | B2 | 7/2013 | Palreddy et al. |
| 8,565,878 | B2 | 10/2013 | Allavatam et al. |
| 8,600,489 | B2 | 12/2013 | Warren et al. |
| 8,670,826 | B2 | 3/2014 | Warren et al. |
| 8,706,215 | B2 | 4/2014 | Kaib et al. |
| 8,712,523 | B2 | 4/2014 | Sanghera et al. |
| 8,831,711 | B2 | 9/2014 | Freer et al. |
| 8,983,586 | B2 | 3/2015 | Zhang |
| 9,119,596 | B2 | 9/2015 | Sanghera et al. |
| 9,352,165 | B2 | 5/2016 | Zhang |
| 9,924,885 | B2 | 3/2018 | Stadler et al. |
| 2004/0225329 | A1 | 11/2004 | Wagner et al. |
| 2006/0069322 | A1 | 3/2006 | Zhang |
| 2008/0172100 | A1* | 7/2008 | Sanghera ............ A61B 5/04011 607/30 |
| 2008/0269813 | A1 | 10/2008 | Greenhut et al. |
| 2012/0046563 | A1 | 2/2012 | Allavatam et al. |
| 2015/0224322 | A1 | 5/2015 | Gunderson |
| 2015/0305637 | A1* | 10/2015 | Greenhut ........... A61B 5/04011 600/512 |

OTHER PUBLICATIONS

International Search Report and Written Opinion dated Jan. 31, 2017 for International Application No. PCT/US2016/057825.

\* cited by examiner

MULTI-VECTOR SENSING IN CARDIAC DEVICES USING A HYBRID APPROACH

CROSS REFERENCE TO RELATED APPLICATIONS

The present application claims the benefit of and priority to U.S. Provisional Patent Application Ser. No. 62/245,757, titled SIGNAL QUALITY MONITORING FOR MULTIPLE SENSE VECTORS IN CARDIAC DEVICES, U.S. Provisional Patent Application Ser. No. 62/245,738, titled MULTI-VECTOR SENSING IN CARDIAC DEVICES WITH SIGNAL COMBINATIONS, U.S. Provisional Patent Application Ser. No. 62/245,762, titled MULTI-VECTOR SENSING IN CARDIAC DEVICES WITH DETECTION COMBINATIONS, and U.S. Provisional Patent Application Ser. No. 62/245,729, titled MULTI-VECTOR SENSING IN CARDIAC DEVICES USING A HYBRID APPROACH, each filed on Oct. 23, 2015, the disclosures of which are incorporated herein by reference.

BACKGROUND

A number of cardiac rhythm management products are available for the use in diagnosis and treatment of various conditions. These may include, for example, subcutaneous, transvenous, or intracardiac therapy devices such as pacemakers, defibrillators and resynchronization devices. Implantable, external and/or wearable cardiac monitors are also available. External or wearable therapy products may include defibrillator vests and external pacemakers, as well as automatic external defibrillators.

In some cardiac rhythm management products, a plurality of sensing electrodes may be provided for use in obtaining cardiac electrical signals for analysis of the patient's cardiac status. Some such products have sufficient sensing electrodes to define more than one sensing vector, with each sensing vector defined by a combination of 2 or more electrodes. Some devices select a preferred sensing configuration as the "best" vector for use in observing cardiac conditions. Some proposed solutions use data from multiple vectors simultaneously. New and alternative approaches to the use of data from multiple sensing vectors are desirable.

OVERVIEW

The present inventors have recognized, among other things, that a problem to be solved is the need for new and alternative approaches to the use of multiple sensing vectors in cardiac devices. In some examples, a device is configured to use a preferred sensing configuration, and data illustrating signal quality for the preferred sensing configuration is monitored. If the preferred sensing configuration signal quality degrades, other sensing vector data is analyzed and different sensing vector is selected to replace the preferred sensing configuration from a first default to a new, updated default. Prior to making a switch, certain conditions or limits may be applied by, for example, requiring that the patient cardiac rhythm be stable. Initialization may be performed when bringing the new sensing vector online.

In some examples, a switch from an initial preferred sensing configuration to a replacement or "better" sensing vector configuration can be performed in response to detection of signal quality degradation in the initial preferred sensing configuration. Reversion to the original preferred sensing vector may be performed once signal quality improves in the preferred sensing vector, if certain conditions are met. In an example, the preferred sensing vector uses data from a single sensing vector, while the better sensing vector configuration may use data from a different sensing vector, data from multiple sensing vectors, or data from the same sensing vector but with different parameters for filtering, amplification or data processing. If the signal quality of the initial preferred sensing configuration does not improve, a flag or warning may be issued suggesting that a user of the device (which may be wearable or implantable, for example) should seek medical attention.

Switching may follow initialization of the replacement or "better" sensing vector configuration. The patient may be alerted or the patient's status may be checked prior to switching sense vector configurations to ensure the patient is not in a treatable or potentially treatable state, for example.

In some examples, a switch of the sensing vector configuration is temporary in nature. However, to prevent repeated switching or loss of signal quality, in some examples, prior to reversion to an initial or original preferred sensing configuration, a determination may be made as to whether a timer set upon switching of the sensing vector configuration has expired. In a further example, the timer setting is modified in response to repeated sensing vector configuration changes.

This overview is intended to provide a summary of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
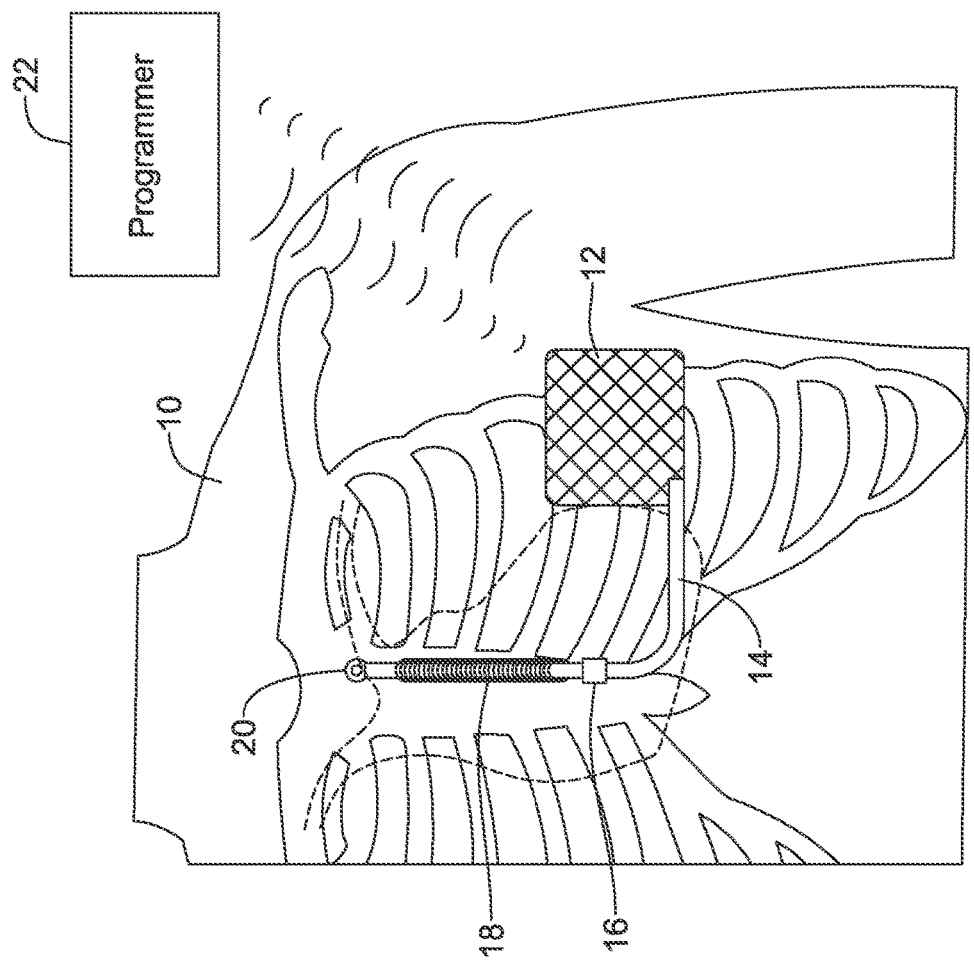
FIG. 1 shows an illustrative implantable medical device system with multiple sensing vectors available.

FIG. 1 shows the S-ICD System™ from Cameron Health, Inc., and Boston Scientific Corporation as implanted in a patient. The system is implanted in a patient 10 with a canister 12 in the left axilla at about the level of the cardiac apex. A lead 14 is placed subcutaneously, beneath the skin and over the ribcage of the patient, with a first portion extending along the inframammary crease to the xiphoid, and then superiorly parallel to and about 1-2 cm to the left of the sternum. A proximal sense electrode 16, shocking coil electrode 18, and distal tip sense electrode 20 are provided along the parasternal portion of the lead 14. The entire system is implanted outside of the ribcage.

The canister 12 may further include such components as would be appropriate for communication (such as RF communication, inductive telemetry or other suitable communication linkage) with an external device such as a programmer 22 or a bedside or home monitoring device. For example, during an implantation procedure, once the canister 12 and lead 14 are placed, the programmer 22 may be used to activate the canister 12 and/or direct/observe diagnostic or operational tests. After implantation, the programmer 22 may be used to non-invasively determine the status and history of the implanted device. The programmer 22 in combination with the canister 12 may also allow annunciation of statistics, errors, history and potential problems to the user/medical practitioner, and may also allow for updating of programming in the canister 12.

There several individual and combinational sensing vectors available with this implantation. In the commercial implementation there are three available sensing vectors: between electrode 16 and electrode 20, between electrode 16 and the metal housing of the canister 12, and between electrode 20 and the metal housing of the canister 12. If desired, the system could also be modified to use electrode 18 as a sensing electrode, paired with any of electrodes 16 and 20 or the metal housing of the canister 12. Moreover, it would be possible to combine two electrodes as a single pole for sensing, if desired.

The illustration in FIG. 1 is just one example. In additional examples, an implantable or wearable cardiac monitor may have multiple electrodes on a housing and/or lead to define two or more sensing vectors. Leadless devices, such as leadless cardiac pacemakers for implantation inside the heart, may have multiple sensing electrodes on or extending from a canister or housing to define multiple sensing vectors. Wearable defibrillators or pacemakers may also provide multiple cutaneous electrodes on the anterior and/or posterior thorax of the patient, and may even include indifferent electrodes elsewhere such as on a limb. Additional sensing data may be mathematically derived from combinations of the physical vectors provided by the sensing electrodes. Transvenous and/or epicardial implantable devices may have an active housing adapted for use in sensing along with plural electrodes for sensing on one or more leads, as is well known in the art. For example, a transvenous device may have a right ventricular lead with atrial and ventricular sensing electrodes as well as an indifferent electrode on the canister.

For any of these systems, the availability of multiple sensing vectors poses several questions, including how to determine which of several sensing vectors is or is not performing well, and how to decide whether to switch from one sensing configuration to another. The first generation of the S-ICD System shown in FIG. 1 incorporated sensing vector selection methods operable in the clinical setting while in communication with a programmer. Some details of such methods are discussed in U.S. Pat. Nos. 7,392,085, 7,623,909, and 8,200,341, the disclosures of which are incorporated herein by reference. The device did not automatically switch sensing vectors in response to identified sensing signal quality metric changes.

Some additional background discussion of the use of multiple vectors and sensing therewith is shown in U.S. Pat. No. 5,313,953, as well as U.S. Pat. No. 5,331,966 which additionally shows a device with multiple housing electrodes for sensing. While these prior discussions identify the possibility of ambulatory vector quality monitoring and switching, and/or combining multiple sense vector signals together, there remains additional need for alternatives and new devices and methods to perform signal quality monitoring, sense vector switching, and/or to provide for combining multiple sense vectors together.

Figure 2:
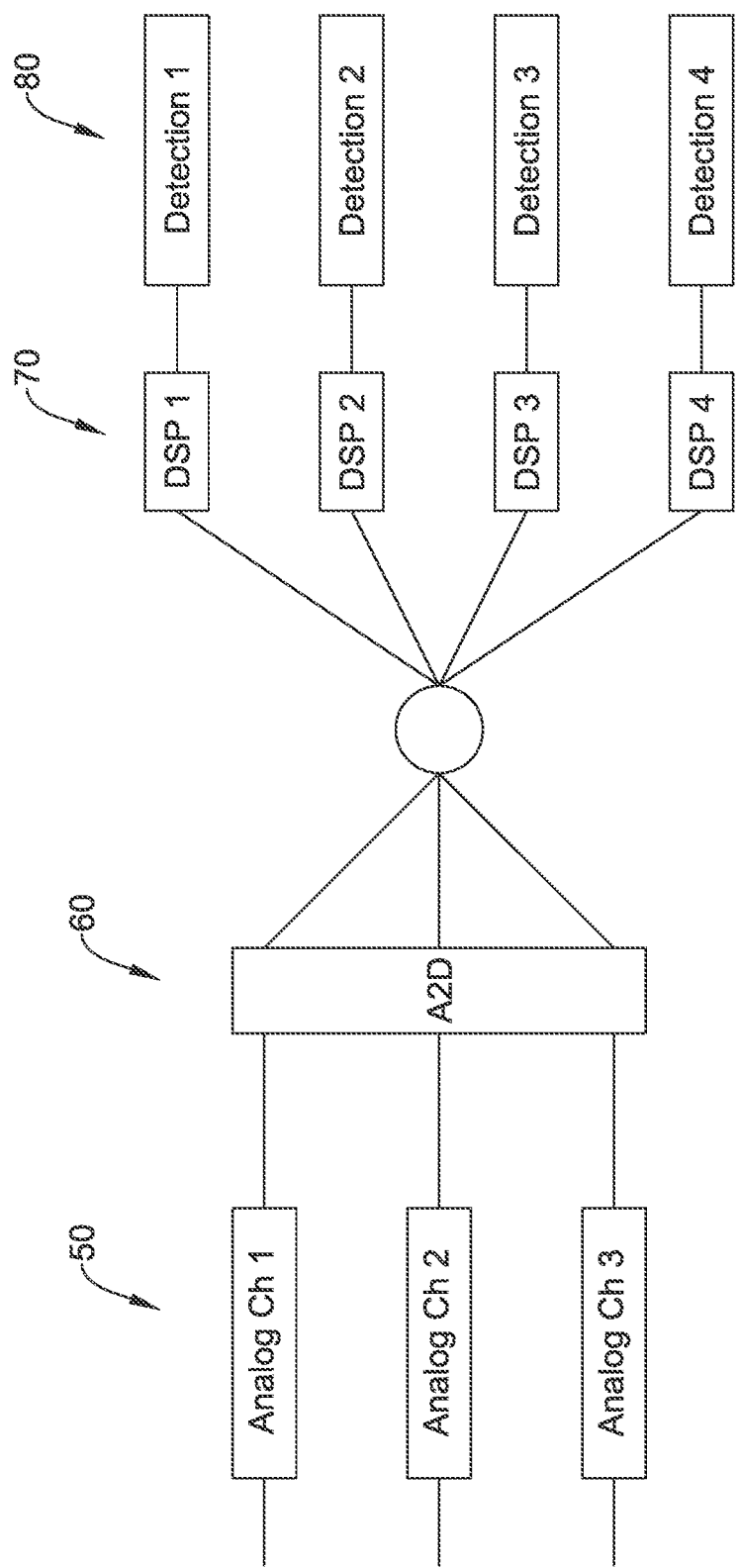
FIG. 2 shows schematically an illustrative input circuit design.

FIG. 2 shows an illustrative sensing input system. A plurality of analog input channels are defined as indicated at 50. The analog channels 50 may be dedicated or hard wired to a particular combination of sensing electrodes, or may defined using a multiplexor or other switch array to couple to pairs or groups of sensing electrodes such as described above and/or in association with FIG. 1. The individual channels may include DC blocking, bandpass, notch, bandstop, 50/60 Hz blocking, and/or other filtering circuitry as well as amplification circuitry such as a low noise amplifier, either as stand-alone circuits or operating cooperatively with an analog to digital conversion (ADC) circuitry 60. Any suitable ADC circuitry may be used, including a wide array of devices known in the art including delta-sigma, successive approximation, Wilkinson, ramp-compare, delta encoded, pipeline, integrating, etc.

In some examples only a subset of the analog channels 50 are converted at any given time; in other examples all of the analog channels 50 may be converted. The plurality of digital signals output by the ADC circuit can be assessed on one or plural digital signal processors (DSP) 70, or may be analyzed together in single processor. For power saving purposes, and to take advantage of modular design, it may be suitable to use dedicated DSP to yield a digital signal for use in detection circuits 80. Any suitable DSP circuit can be used at 70.

One element of DSP may be the inclusion of a digital filtering circuit to narrow the band of signals to a range generally between about 10 and 40 Hz, though wider or narrower ranges may be used. In addition, line signal filtering at 50 or 60 Hz, depending on geography, may be implemented in the DSP. In some examples, a DSP may have five filter stages with each stage being a configurable bi-quad filter, or other filter. One or more stages may be used for 50 and 60 Hz notch filters to eliminate line noise. A bandpass can be generated with two other stages by having a low pass filter in the range of 15-40 Hz, or about 25 Hz in another example, and a high pass filter in the range of 1 to 15 Hz, with 9 Hz serving as one example. Where multiple signals are processed in parallel, not all signals will necessarily be filtered the same. In some examples, a single channel of incoming signal may be assessed using two different filtering methods, with the two separate outputs from the single source processed in parallel.

In some examples the individual detection blocks at 80 each use a separate cardiac cycle detection method to identify heart beats for use in one or more of defining a cardiac cycle signal for morphology (shape) analysis, and or to count cardiac cycles per unit time to generate a cardiac rate for a given chamber of the heart. Individual detection blocks at 80 may each use the same method of cardiac cycle analysis, or different methods may be selected for different digital signals. For example, if one detection line is configured for use on a signal captured using two intracardiac electrodes, and a different detection line uses signal captured using two subcutaneous electrodes, the detection lines would likely each use a different mode of detection, as the intracardiac signal will look quite different from the subcutaneous signal. Some examples of cardiac cycle detection (also sometimes referred to as R-wave or beat detection) are shown in U.S. Pat. Nos. 8,565,878 and 5,709,215, the disclosures of which are incorporated herein by reference. Several methods are known in which a time varying threshold compared against the received cardiac signal until the threshold is crossed, at which point a beat or new cardiac cycle may be declared.

Figure 3:
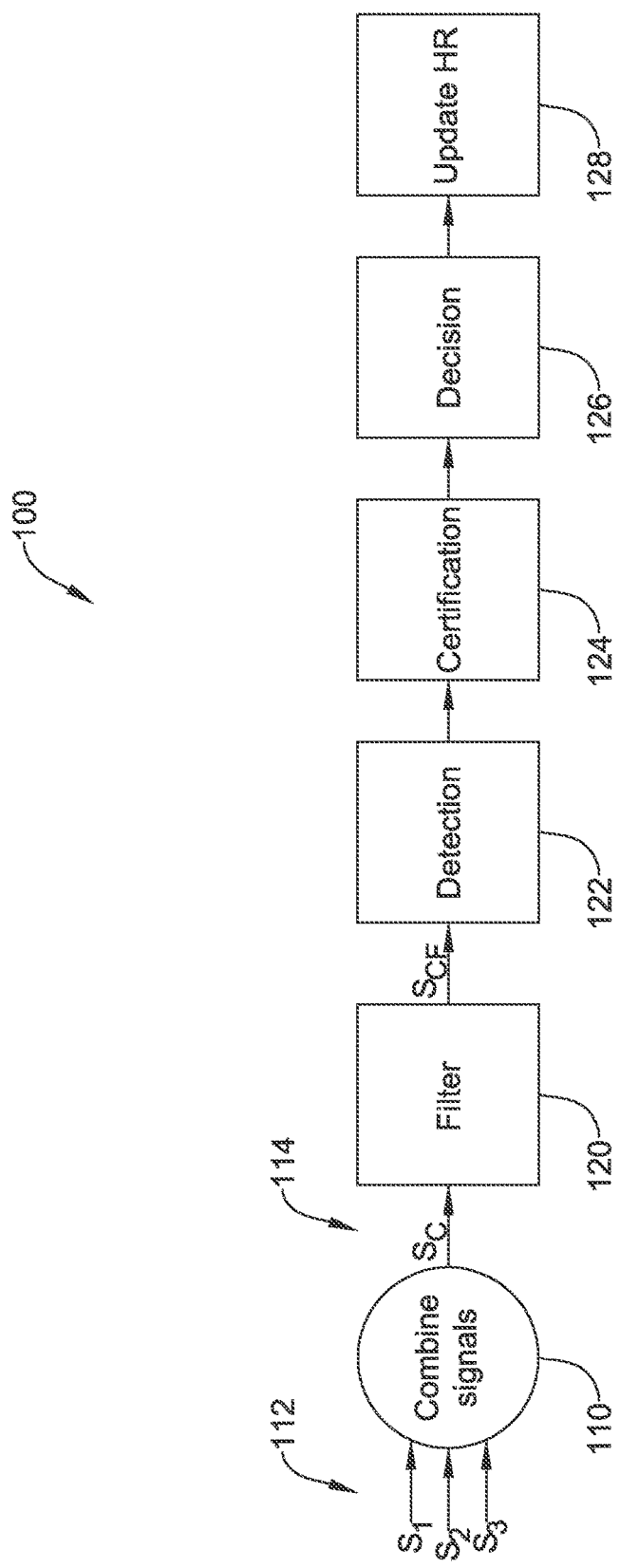
FIG. 3 shows an illustrative multi-vector analysis in block flow form.

FIG. 3 shows an illustrative method of combining multiple vector signals together. The illustrative method 100 begins by combining signals, as indicated at 110, to convert three data streams S1, S2, S3, indicated at 112, into a combined data stream Sc, as shown at 114. When combining the signals, a plurality of weighting factors may be applied to provide different weights to each data stream, for example as described in U.S. Provisional Patent Application Ser. No. 62/245,738, titled MULTI-VECTOR SENSING IN CARDIAC DEVICES WITH SIGNAL COMBINATIONS, and U.S. Provisional Patent Application Ser. No. 62/245,762, titled MULTI-VECTOR SENSING IN CARDIAC DEVICES WITH DETECTION COMBINATIONS, the disclosures of which are incorporated herein by reference. The weighting factors may be applied to the analog domain signal for example by using adjustable gain circuitry in the input prior to analog-to-digital conversion. Weighting factors may be applied during analog-to-digital conversion, or on the digital signal after analog-to-digital conversion.

This combined data stream is then filtered at 120, for example to a bandpass in the range of 3 to 40 Hz, or more preferably about 9 to 25 Hz, or other ranges as suited for a particular application. Filtering 120 may be performed in association with amplification and may be performed on either an analog signal or a digital signal, or both. Filtering may further include DC blocking filters and/or the application of a notch filter(s) to take out 50 and/or 60 Hz line noise.

The filtered combined signal (indicated as $S_{CF}$) goes to a detection stage at 122, where individual cardiac cycles or beats may be detected. For example, an amplitude or magnitude measure generated using the combined signal can be compared to a detection threshold, wherein the detection threshold may be a time varying threshold. Upon crossing of the detection threshold, a new cardiac cycle may be declared.

Individual detected cardiac cycles, standing alone or in small groups, or as a series of detections of cardiac cycles, may then go through a certification stage 124. Certification 124 may include, for example, analyzing one or more signals to determine whether there is noise in the signal, or analyzing detected events in pairs or small groups or as a series to determine whether any overdetected events have taken place. An overdetected event may occur if/when multiple cardiac cycles are declared but only one such cycle took place, or if a cardiac cycle is declared without a new cardiac cycle having occurred.

Upon removal of noise and overdetections, the certified cardiac cycles are passed to a decision phase 126 which may use one or more of the rate at which cardiac cycles are detected and/or the morphology (shape) of the cardiac signals associated with cardiac cycles to determine whether a treatable or otherwise targeted cardiac state is occurring. The decision phase 126 may include updates to the heart rate 128.

In block 110, in an example and assuming three sensing vectors (though more or fewer can be used), the combined data stream Sc can be calculated as using this formula:

$$S_c = k_1 * S_1 + k_2 * S_2 + k_3 * S_3 \quad \text{(Formula 1)}$$

In this equation, each of the k-factors is a weighting factor, and each S1 represents a particular individual sensing vector signal. The weighting factor may be determined by consideration of one or more signal quality metrics such as amplitude, signal-to-noise ratio, variability or stability, consistency of shape, polarity correction, noise burden, and likelihood of oversensing or other malsensing, for example. The weighting factors may be updated periodically or in response to identified conditions.

The combining step at 110 may instead appear at different points in the diagram, for example, after filtering 120, detection 122, certification 124, and/or decision 126. In some examples parallel processing allows both individual sensing vector analysis and combined signal analysis to be performed in multiple, separate channels, with cross checking at each or several of the stages 120/122/124/126/128. Further details may be found in U.S. Provisional Patent Application Ser. No. 62/245,738, titled MULTI-VECTOR SENSING IN CARDIAC DEVICES WITH SIGNAL COMBINATIONS, and U.S. Provisional Patent Application Ser. No. 62/245,762, titled MULTI-VECTOR SENSING IN CARDIAC DEVICES WITH DETECTION COMBINATIONS, the disclosures of which are incorporated herein by reference.

Figure 4:
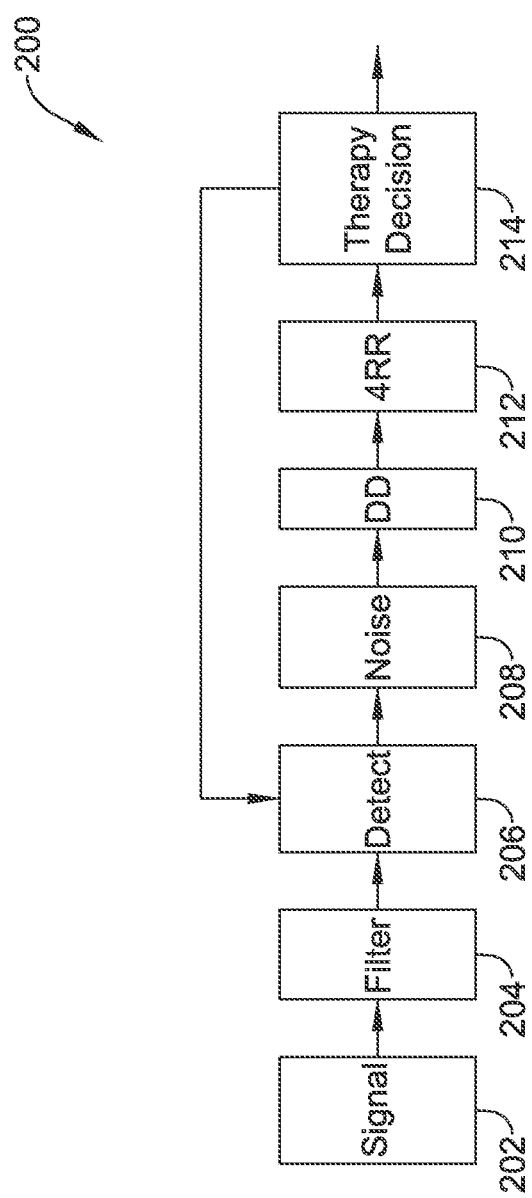
FIG. 4 shows an illustrative cardiac rhythm analysis method in block flow form.

FIG. 4 shows an illustrative cardiac rate calculation method in block flow form. The method 200 takes an incoming signal 202 and applies filtering at 204. Illustrative filtering 204 may include bandpass filtering to get the cardiac signal and notch filtering to omit 50/60 Hz line noise. Cardiac cycle detection is performed at 206, and may include R-wave detection, QRS detection, or other detection. While some systems focus on ventricular signals, other systems may be designed to detect atrial signals, such as P-waves, alone or in addition to the ventricular signal.

Noise may then be analyzed at 208 to eliminate any detections caused by or largely infected with noise. Overdetection or double detection analysis may be performed at 210. Some illustrative examples for noise and overdetection analysis 208, 210 are shown, for example, in U.S. Pat. No. 8,185,198, titled METHOD AND DEVICES FOR PERFORMING CARDIAC WAVEFORM APPRAISAL (noise), and U.S. Pat. Nos. 8,160,687 and 8,160,686, both titled METHODS AND DEVICES FOR ACCURATELY CLASSIFYING CARDIAC ACTIVITY (overdetection), the disclosures of which are incorporated herein by reference.

Finally, a 4RR average 212 is calculated for this example, where four detected cycles are assessed as a group (they need not be consecutive, although the four cycles often are when sensing is working well) to calculate an estimate of cardiac rate. Other numbers of cycles/detections may be used, from a single cycle up to eight or more. Rather than a 4RR average, which would be ventricular in nature, a 4PP average may instead be used, for example, to estimate atrial rate.

The process may take a rate estimate from block 212 for use in making therapy decision 214, or, for non-therapy systems such as monitoring devices, determinations of whether to store data for later use, such as when a cardiac condition of interest (bradycardia, tachycardia, asystole, etc.) appears, or to provide an alert to a patient or to an external system. In some examples, the incoming signal 202 is filtered 204 on a more or less continuous basis as an incoming data stream, with the detection block 206 (which may be implemented by an ASIC) providing wakeups to a controller to perform steps involving noise and/or double detection, though other architectures may be used instead.

Figure 5:
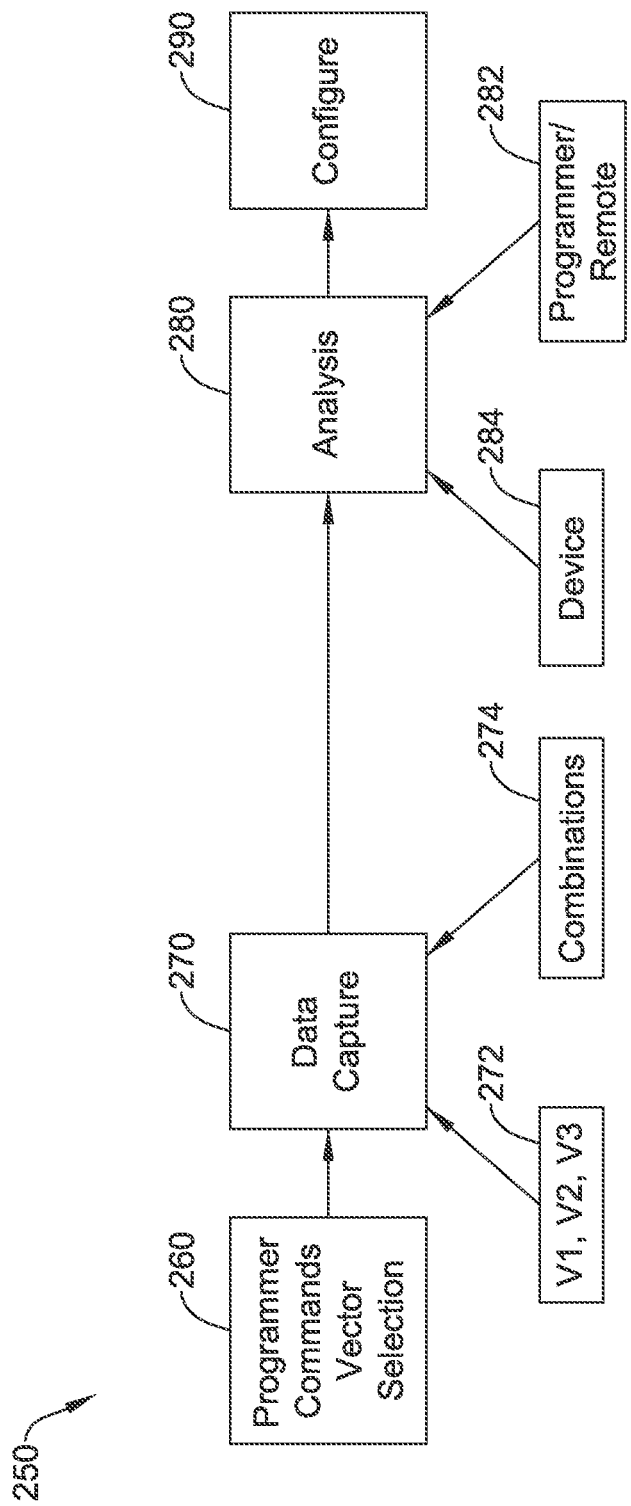
FIG. 5 shows an illustrative sensing vector selection method in block flow form.

FIG. 5 shows an illustrative sensing vector selection method in block flow form. In this method, 250, a programmer commands vector selection at 260, as may be the case for an in-clinic examination. In other examples, the programmer may be a patient controlled device such as a patient controller, at home programmer, or bedside monitor, or even as the technology moves forward, the patient's mobile device such as a tablet computer or cell phone. In still other examples, vector selection may autonomously be performed by an implanted or wearable system.

Data capture is then performed at 270. In some examples, data capture is prospective where a device, whether implantable or wearable, begins capturing data for vector selection upon receiving a command or making an autonomous decision to perform vector selection. In other examples, data looping may be facilitated by the device such that once a decision is made to begin vector selection, already captured data can be reviewed. Such data may include data from a plurality of individual sensing vector such vectors V1, V2, V3 (noted at 272), or using combinations of such vectors as noted at 274.

The captured data from 270 can be analyzed at 280 by, for example, a programmer or remote computer 282 or the device itself 284. During such analysis, one or more features of the sensed signal of the vectors or combinations under review may be assessed using one or more metrics such as signal to noise ratio, stability/variability, amplitude, etc. A preferred configuration is then selected as noted at 290. In some examples, a best vector may be selected using methods discussed in U.S. Pat. Nos. 9,119,596, 7,783,340, 7,392,085, 7,330,757, and/or 5,331,966, the disclosures of which are incorporated herein by reference. In addition, the analysis at 280 may also rely on factors noted in U.S. Provisional Patent Application Ser. No. 62/245,757, titled SIGNAL QUALITY MONITORING FOR MULTIPLE SENSE VECTORS IN CARDIAC DEVICES, the disclosure of which is incorporated herein by reference.

Once a preferred vector configuration is identified via the analysis at 280, the device may then be configured to use the preferred vector configuration at 290. Configuration may include storing values for filtering (such as the coefficients for digital filters), and storing switch configurations for selectively coupling input signals to amplifiers and the like for signal processing. Configuration may, in some examples, include storing coefficients for use in Formula 1 (above), to select a combination of sensing vector signals and/or to set the k-values (weights) for deselected sensing vectors to zero.

Figure 6:
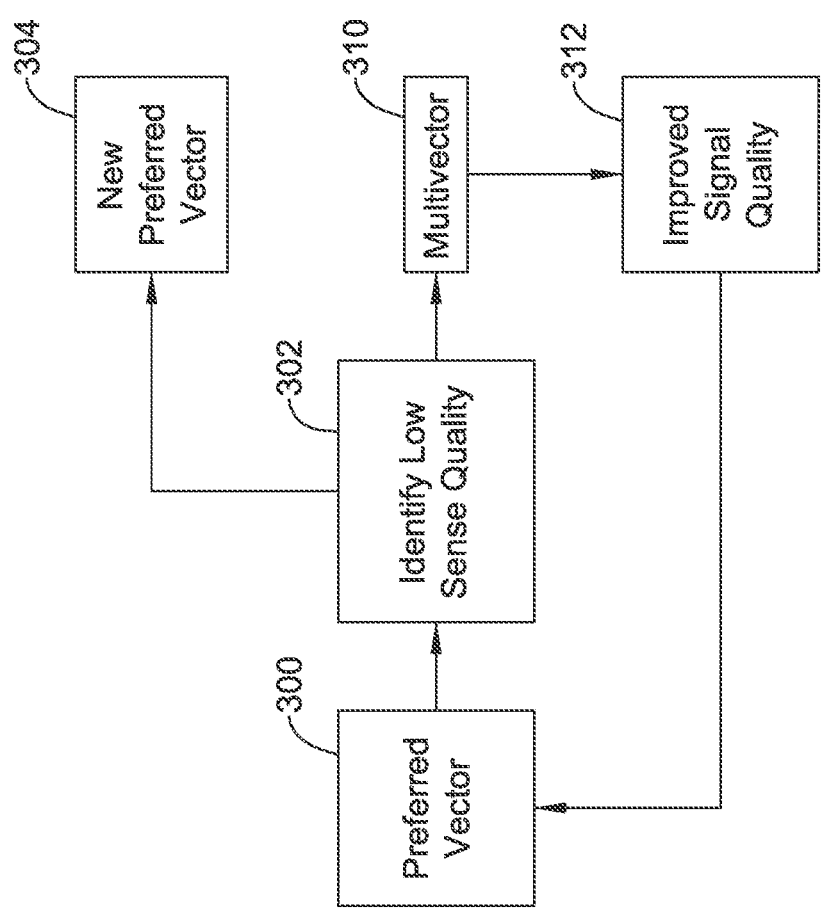
FIGS. 6-10 show illustrative methods in block flow form.

FIG. 6 shows another example in block flow form. In this example, a preferred vector is selected for ongoing cardiac signal analysis at 300. Such a preference may be determined by selecting a "best" sensing vector using metrics such as signal to noise ratio, baseline stability, desired event amplitude, or other factors noted in U.S. Provisional Patent Application Ser. No. 62/245,757, titled SIGNAL QUALITY MONITORING FOR MULTIPLE SENSE VECTORS IN CARDIAC DEVICES, the disclosure of which is incorporated herein by reference. The selection of and monitoring of a single vector may reduce power consumption relative to a multi-vector analysis. The use of a preferred vector 300 may be described as implementing a preferred sensing configuration.

The next step as shown at 302 is to determine whether a low quality signal is found for the preferred vector. Low quality signal may be determined by reference to the sensed signal itself by observing metrics such as the frequency content of the signal, whether baseline is consistently maintained, signal-to-noise ratio (SNR), peak amplitude. Low quality signal may also be determined by reference to analysis of cardiac cycle detections using, for example, noise and overdetection analysis (Blocks 208, 210 of FIG. 4), where a low quality signal may be found if noisy or overdetected cardiac cycles are found to be occurring.

When a low quality signal is identified at 302, this may trigger reassessment of the preferred vector at 304, optionally. In some examples, rather than jumping to change vectors at 304, the method instead may go to a multi-vector analysis 310. The multivector analysis 310 may use Formula 1, for example, and/or methods disclosed in U.S. Provisional Patent Application Ser. No. 62/245,738, titled MULTI-VECTOR SENSING IN CARDIAC DEVICES WITH SIGNAL COMBINATIONS, U.S. Provisional Patent Application Ser. No. 62/245,762, titled MULTI-VECTOR SENSING IN CARDIAC DEVICES WITH DETECTION COMBINATIONS, the disclosures of which are incorporated herein by reference. Continuously, periodically, or occasionally, the signal quality of the preferred vector may be reassessed, and if/when the signal quality of the preferred vector improves as 312, the analysis may return to using the preferred vector 300.

Figure 7:
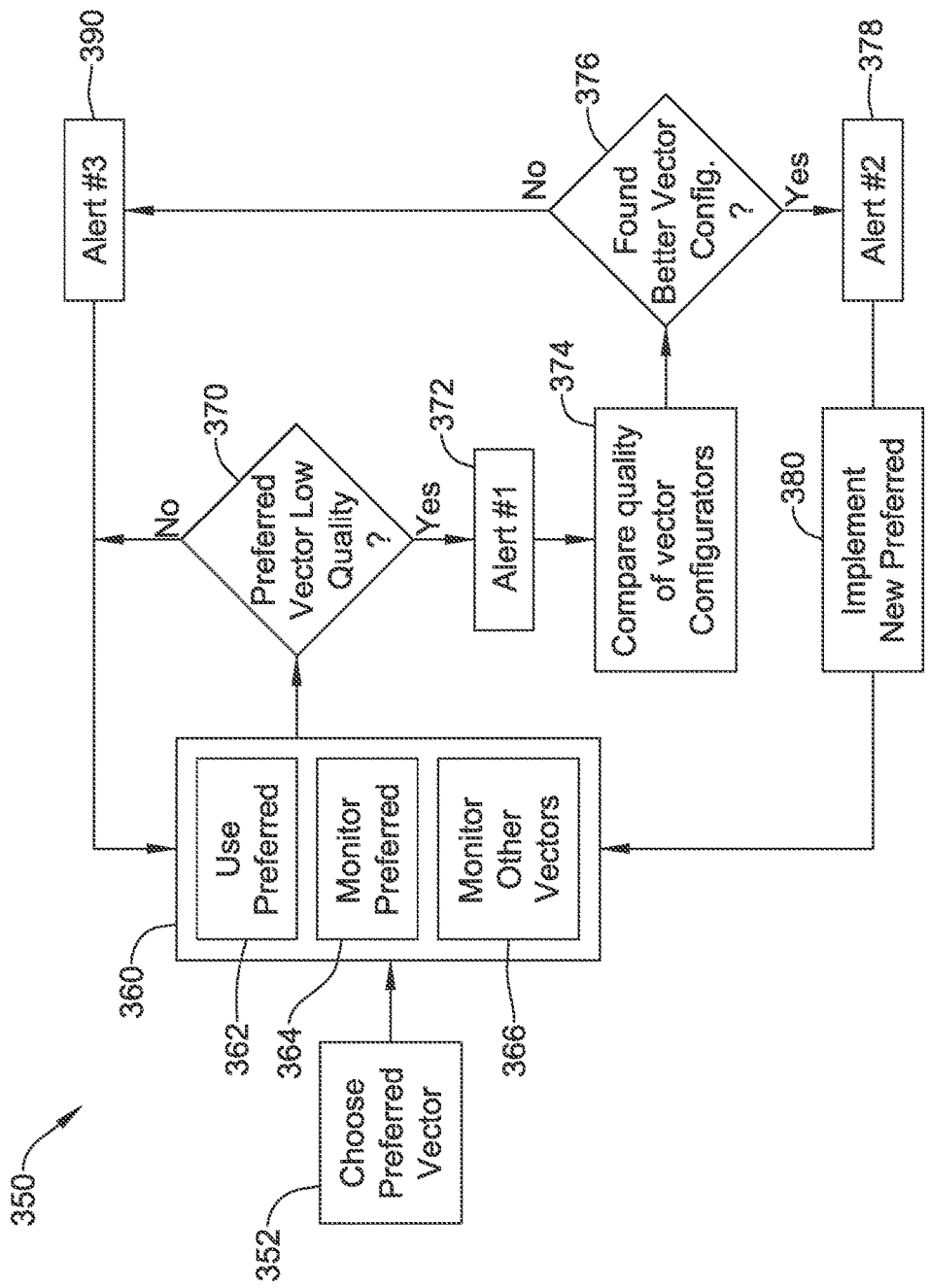

FIG. 7 shows an illustrative method for switching sensing vector configurations in block flow form. The illustrative method 350 presumes that a preferred vector has been chosen at 352, using for example methods described above. From block 352, a normal operation block at 360 is shown as including the use of the preferred sensing vector configuration 362 for cardiac signal analysis. Intermittently or continuously the signal quality of the preferred sensing vector configuration is monitored as noted at 364. In addition, intermittently or continuously the sensed signal quality of other vectors or vector configurations is also monitored at 366. For example, blocks 364 and 366 may alternate according to a schedule, or both may be performed simultaneously.

From time to time, for example on a periodic or occasional basis, the method determines whether the preferred sensing vector illustrates low quality signal at 370. If low quality signal is found at block 370, a first alert may issue at 372. The first alert 372 may indicate to a patient, physician, remote monitor, programmer, etc., or to the device itself that low quality sensing with the primary sensing configuration is taking place. Next the quality of available sensing vector configurations is compared at 374. If a better vector configuration is found in the analysis at 374, then block 376 directs the method to generate a second alert at 378.

The second alert 378 may indicate to a patient, physician, remote monitor, programmer, etc., or to the device itself, that a change in preferred sensing vector configuration is to be performed. Such an alert may, for example, prompt a patient to provide a feedback signal if the change is not wanted, or to stop what he or she is doing and sit still while the vector change takes place, for example. In other examples, the alert 378 may issue to a remote station via the internet or cellular towers, for example, to provide a nurse or physician the opportunity to review data related to the potential change in sensing vector and confirm, in systems facilitating remote interaction with a cardiac rhythm management device. After the second alert 378 is issued and, if called for, acknowledged, the device implements a new preferred vector configuration at 380, and returns to the ordinary operation block 360 using the new preferred vector configuration.

Going back to block 376, if there is no identified "better" sensing vector configuration from the analysis at 374 than the one that showed low quality at block 370, a third alert may be issued at 390. The third alert 390 may indicate to a patient, physician, remote monitor, programmer, etc., or to the device itself, that sensing is of low quality and the patient may be at risk of malsensing, where malsensing may include failure to properly identify a cardiac condition, individual cardiac cycles, or may lead to inappropriate therapy or a failure to deliver needed therapy.

In some examples the nature of the alert in any of blocks 372, 378, 390 may provide information as to why the low quality sensing has been identified. For example, if a device identifies noise on the preferred sensing vector at block 370, and also finds noise on other sensing vectors at block 374, the third alert 390 may suggest that the patient move away from potential sources of electromechanical interference (EMI), since some EMI sources can impair all sensing vectors of a given device. In another example, one or more alert may request that the patient make note of or record their current posture or activity to assist a physician in later troubleshooting any sensing signal quality issues. In another example, one or more of the alerts may request that a patient at least momentarily cease activity, or assume a particular posture such as sitting, standing or laying down, to allow the implantable system to self-diagnose a sensing quality issue as being related to patient activity, exercise or specific posture.

The first alert 372, second alert 378, and third alert 390 are each optional and may be included or omitted in various combinations in some embodiments. In some examples, the first alert is internal to the cardiac rhythm management device itself, while the second or third alerts are provided externally or as annunciating signals (audible, visible or buzzing/vibrating/tactile) to a patient. In some examples, only the third alert 390 is provided externally of the device, the first alert 372 is stored internally to a device, and second alert 378 is omitted.

Following the third alert 390, or if the sensing quality is not low at block 370, the method returns to the ordinary operation block 360 continuing to use the previously selected preferred sensing vector configuration.

Figure 8:
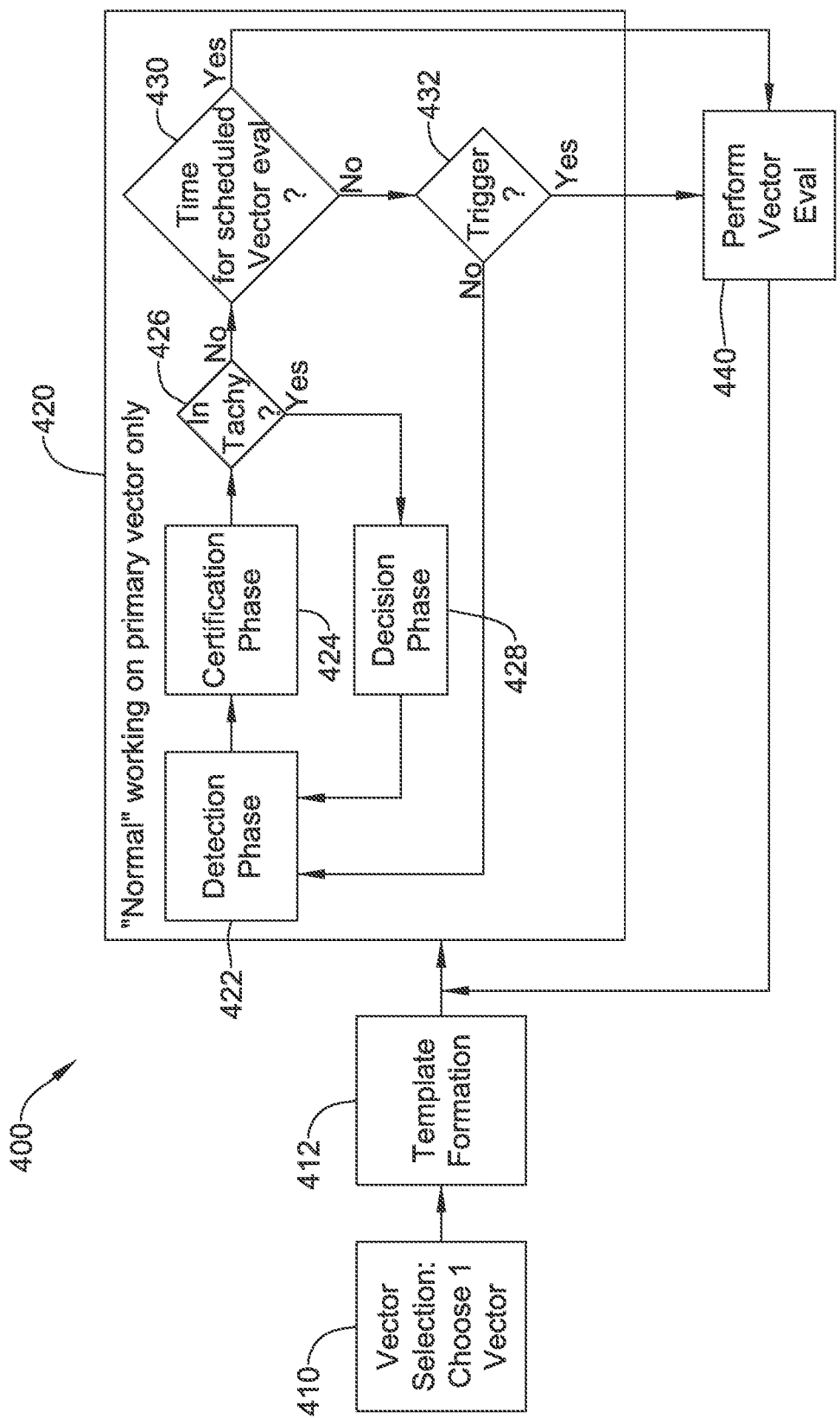

FIG. 8 shows an illustrative method for triggering the analysis of sensing vectors in block flow form. The method 400 in FIG. 8 may use either a trigger of low sensing quality, or may reference periodic evaluation of the sensing vector configuration. Here, a primary sensing vector configuration is chosen at 410, which may select a single sensing vector. Alternatively, the selection at 410 may identify weighting values for a combined signal analysis.

To initialize the use of the selected sensing vector configuration, the method next forms a template, which may be a normal sinus rhythm template, at block 412. For example, template formation as described in U.S. Pat. No. 7,376,458, titled METHOD FOR DEFINING SIGNAL TEMPLATES IN IMPLANTABLE CARDIAC DEVICES, may be used for template formation 412. In another example, the template may be formed using methods described in, for example, U.S. Pat. No. 6,728,572 or U.S. Pat. No. 6,393,316, among other examples of template formation.

Next, the method makes use of the preferred sensing vector configuration in block 420 to analyze the cardiac signals of the patient. This may include detection 422 and certification 424, where certification may combine noise and overdetection analysis, or use other features to review individual detected cardiac cycles and certify those that appear to be true detections of desired signals.

The certified detections are used to determine whether the patient is experiencing a tachycardia ("in tachy"). If the patient is found to be in tachy, suggesting the potential need for therapy and/or that the analysis of cardiac signals may be somewhat degraded simply by virtue of the patient's rate, the method moves to a decision phase 428. The flow to block 428 avoids placing the device in a state where vector analysis is being performed when therapy is needed. For example, vector analysis could be tainted by the potentially polymorphic nature of some treatable tachycardaia conditions (ventricular fibrillation and/or polymorphic ventricular tachycardia). In another example, a vector analysis could itself delay therapy decisions. The decision phase 428 may use any suitable approach to determining whether therapy is to be delivered, by, for example, using rate and/or discrimination zones to mark and count treatable condition indicators in X/Y filters or number-of-intervals to detect assessments that are known in the art. See, e.g., U.S. Pat. Nos. 7,330,757 and 8,670,826, and US Pre-Grant Patent Publication 2005-0154421, the disclosures of which are incorporated herein by reference, for some discussion of the ways that X/Y filters or NID analysis may be used.

If no tachycardia condition is found at block 426, the method determines whether it is time for a scheduled evaluation of sensing vectors at 430, and/or if a Triggering condition 432 for sense vector analysis is occurring. A Triggering condition 432 may be, for example, a determination that one or more of a drop in sensing signal quality of the preferred sensing configuration, or occurrence of noise detections, or overdetections (recurrent, persistent or continuous for example), is occurring, Another Triggering condition 432 may arise if signal quality monitoring across several vectors is ongoing and a vector that was not selected as a preferred sensing vector has improved in signal quality significantly, to the point where it appears to be superior to the preferred sensing vector. Other Triggering conditions 432 are also identified in U.S. Provisional Patent Application Ser. No. 62/245,757, titled SIGNAL QUALITY MONITORING FOR MULTIPLE SENSE VECTORS IN CARDIAC DEVICES, the disclosure of which is incorporated herein by reference.

If either of blocks 430 and 432 are satisfied, vector evaluation may take place by comparing the available sensing vectors configurations and determining a best or preferred configuration at 440. From block 440, if a new configuration is selected then the template formation at 412 may be performed again or, alternatively, if an existing configuration is kept, then the method simply returns to the ordinary operation block 420. If neither of blocks 430 or 432 call for sense vector configuration evaluation, the method returns to the detection block 422.

In another example, when templates are formed initially at 412, templates may be formed for each of the available sensing vectors in a given system, such that change to the sensing vector per block 440 would not require forming a new sense vector template. On the other hand, it may be desirable for some implementations to attempt template formation whenever vector switching is about to take place, as failure to form a new template (which may occur if the beat-to-beat morphology changes frequently in the newly selected vector) may indicate that the newly selected vector is not as usable as initially determined.

Figure 9:
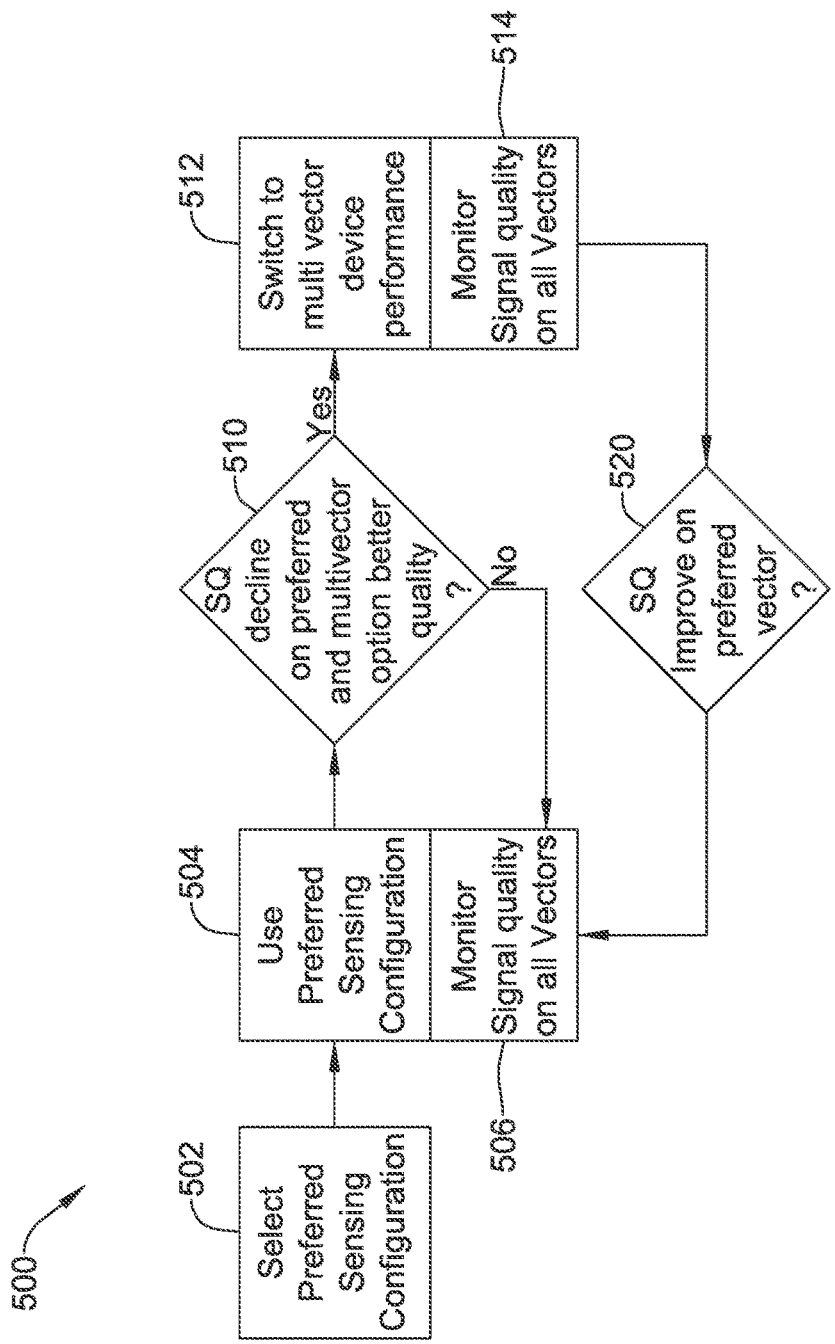

FIG. 9 shows an illustrative method for switching sensing vector configurations in block flow form. In this method 500, again the process begins with the selection and implementation of a preferred sensing configuration 502. The preferred sensing configuration is used at 504 and, meanwhile, signal quality on all sensing vectors is monitored as noted at 506.

Iteratively, continuously, periodically, or in response to a triggering condition, block 510 may be called to determine whether the signal quality has declined on the preferred sensing configuration and, in addition, that a multivector sensing configuration has better sensing quality. If not, the method returns to the parallel blocks 504/506.

If the answer at 510 is yes, then the method switches to using the "better" multivector sensing configuration, as indicated at 512. Meanwhile, as indicated at 514, the signal quality on all vectors is monitored. If and/or when the signal quality improves on the preferred sensing vector configuration, as noted at 520, the system reverts to using the preferred sensing vector configuration with block 504. In some examples, further discussed above and/or below, limitations may be placed on either of the changes called for in blocks 510 and 520.

Looking back at sub-blocks 506 and 514, while "all" sensing vectors are indicated, in some examples instead be "all available" sensing vectors if one or more sensing vectors are flagged, for example by a physician or by a diagnostic test, as being unusable in all cases and therefore unavailable. For example, a physician may flag a sensing vector unusable because the physician has observed that an electrode for the sensing vector is not attached or placed properly, or because the physician has observed actual performance leading to a clinical hazard, such as oversensing and inappropriate shock, for example. A diagnostic test, such as a lead fracture or improper connection test, may flag an electrode as either being misconnected or subject connected via a fractured lead connector (or other failure), making one or more sensing vectors including the flagged electrode entirely unusable.

Figure 10:
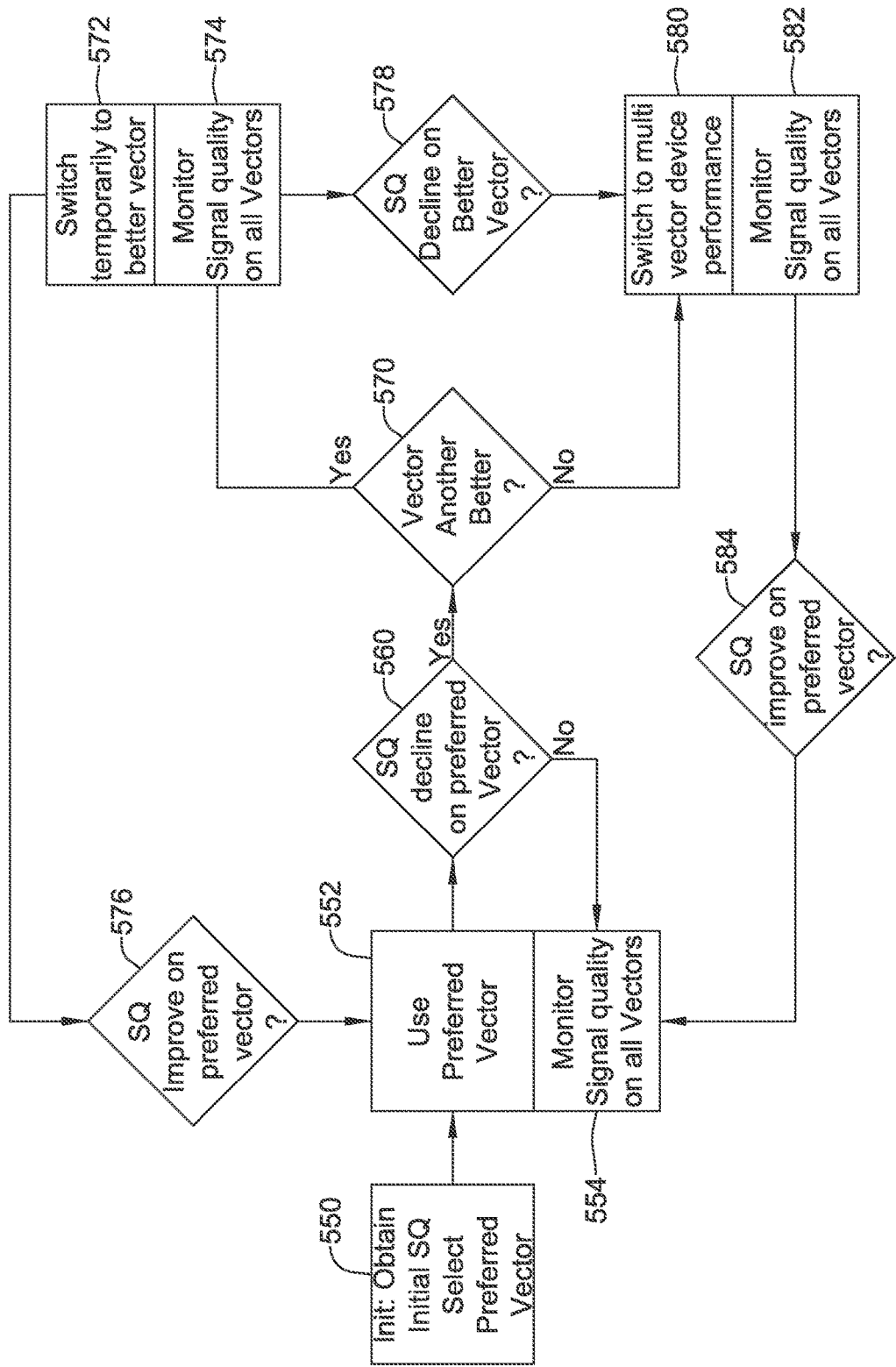

FIG. 10 shows an illustrative method for switching sensing vector configurations in block flow form. This example shows a tiered approach in which single-vector analysis is favored, but multi-vector analysis can be used if the single vectors are not found suitable. In some embodiments, the single vector approach may be favored because processing a single vector of sensing data through detection and subsequent noise and overdetection analysis is likely less power consumptive than multi-vector alternatives.

At block 550, initialization occurs with signal quality obtained for available vectors and selection of a preferred vector. At 552, the preferred vector, which may be a single vector in this example, is used for cardiac signal analysis and, meanwhile (continuously, periodically and/or occasionally), signal quality on other vectors may also be monitored as indicated at 554. At block 560 it is determined whether the signal quality on the preferred vector has declined. If not, the method returns to 552/554.

Whether the signal quality has dropped in block 560 may include comparing signal quality to a threshold. In an example, block 560 combines comparison to a threshold with a determination that malsensing has also occurred (one or more of noise, overdetection, and a long pause suggesting underdetection, for example), and, if so, block 560 is satisfied.

If the signal quality on the preferred vector has dropped at 560, the method next determines whether another (single) vector is better than the preferred vector, as indicated at 570. If a different vector is better, this "better vector" or "better configuration" is implemented temporarily as indicated at block 572, while signal quality continues to be monitored for several vectors as indicated at 574.

The temporary switch at 572 can end in one of two ways in this example. First, if the signal quality on the preferred vector improves, as indicated at 576, the method reverts to using the preferred vector at 552/554. Second, if the signal quality declines on the "better" vector, and the preferred vector has not yet recovered, the system switches to using a multi-vector analysis at block 580.

Multi-vector analysis 580 may be performed as shown and discussed above in relation to FIG. 3, and/or using the methods in U.S. Provisional Patent Application No. 62/245,738, titled MULTI-VECTOR SENSING IN CARDIAC DEVICES WITH SIGNAL COMBINATIONS, U.S. Provisional Patent Application Ser. No. 62/245,762, titled MULTI-VECTOR SENSING IN CARDIAC DEVICES WITH DETECTION COMBINATIONS, the disclosures of which are incorporated herein by reference. In parallel with the multi-vector performance is the monitoring of signal quality on the available sensing vectors noted at 582. If the signal quality improves on the preferred vector, as shown at 584, then the method reverts to using the preferred vector at 552/554. In one alternative, block 582 may instead monitor signal quality on just one vector—the preferred vector. In another alternative, block 582 may be used to trigger recalculation of the multivector analysis 580 if signal quality of one or more sensing vectors changes significantly.

Going back to block 570, having found a signal quality decline in the preferred sensing vector at block 560, the method may find that none of the single vectors have produced a better signal quality than the preferred sensing vector at block 570. If the preferred sensing vector is of low quality at 560, and no other single vector is better at 570, the method again turns to the multi-vector analysis in block 580.

In some examples, block 570 may check not just whether any of the single vectors are better-performing than the preferred sensing vector at a given point in time, but also that the other single vectors are performing better than a threshold of performance. In some examples, block 570 may swap places with block 560, such that a switch of the single vectors occurs when a better single vector is identified. Then, block 560 would be the filter that determines whether to proceed to a multivector approach in blocks 580/582.

In the examples of FIGS. 6-10, as well as FIGS. 13-14, below, signal quality may be a metric based not only on measurable current characteristics of a given sensing vector or sensing vector configuration, but may also take into account trends of the data over time. Examples of the use of trend data are shown in U.S. Provisional Patent Application Ser. No. 62/245,757, titled SIGNAL QUALITY MONITORING FOR MULTIPLE SENSE VECTORS IN CARDIAC DEVICES, the disclosure of which is incorporated herein by reference.

Figure 11:
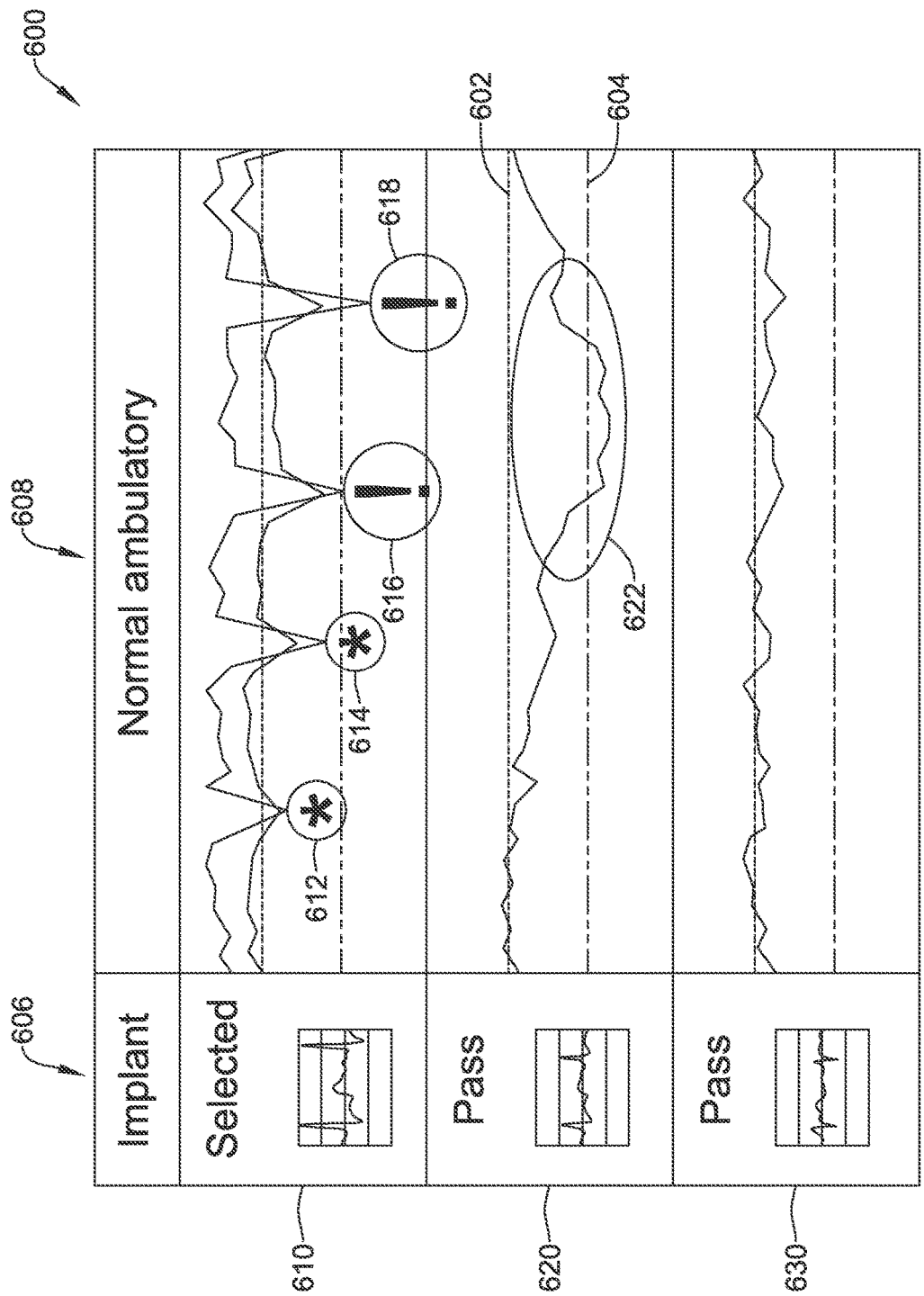
FIG. 11 shows in graphic form sensing vector quality as measured over time and at implant for three sensing vector configurations.

FIG. 11 shows in graphic form sensing vector quality as measured over time and at implant for three sensing vector configurations. The graphic 600 shows sensing signal quality metrics for a trio of sense vectors at 610, 620, 630. The metrics are each compared against high and low performance thresholds 602, 604. As shown at 606, the captured signal at the time of implant was assessed to select one sensing vector as preferred—in this case, a vector having the signal at 610.

During ambulatory activity 608, however, the signal quality of signal 610 drops repeatedly, at 612 and 614 below the higher of the two performance thresholds, and at 616 and 618 below the lower of the two performance thresholds, causing alerts to issue as indicated by the (!) at each of 616, 618. Meanwhile, the performance of the signal at 620 also drops across 622 to below both the upper and lower thresholds for that signal. In some examples, switching off of the preferred, clinically selected sense signal 610 is disfavored unless the lower threshold is crossed, meaning that the sensing vector configuration may only switch to signal 630 at 616 and 618. In other examples, crossing the upper threshold at 612 and 614 may also trigger re-assessment that could select signal 630, at least temporarily, instead of signal 610.

In some examples, the switch to signal 630 would only last so long as the preferred sensing vector (here, signal 610 which was selected at implant as indicated at 606) is inferior to the signal quality of signal 630. Note that in this example, application of the method of FIG. 10 would not likely trigger multi-vector analysis since signal 630 performs better than signal 610 whenever 610 has a drop in signal quality. However, if the upper signal quality threshold is used as a second check on a switch to a different or better single vector, it is possible that multi-vector analysis would be triggered if, for example, at time 616, neither of signals 620, 630 exceed their respective upper thresholds of signal quality.

In other methods, once the decline at one or more of 612, 614, 616, 618 takes place, the preferred vector would be changed from signal 610 to the better performing of 620 or 630. For example, at 612, signal 620 could be selected as a new preferred vector. Later, at 622, signal 630 would become the preferred vector, since at the time signal 620 crosses lower threshold 604, signal 610 is performing poorer than signal 630.

Figure 12:
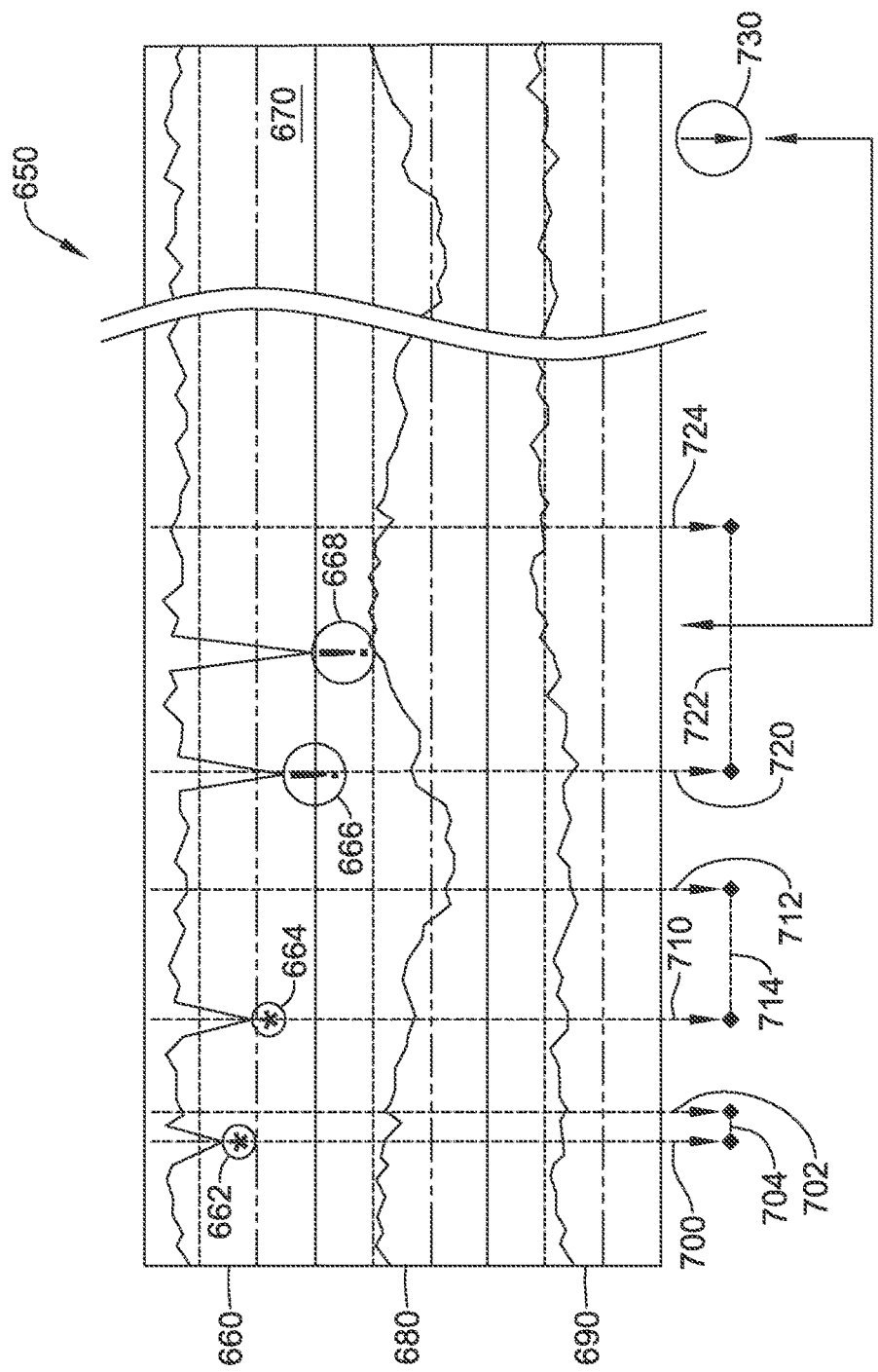
FIG. 12 shows in graphic form operation of a method for switching sensing vector configurations.

FIG. 12 shows in graphic form operation of a method for switching sensing vector configuration. Here, signal quality is shown for each of three signals, 660, 680, 690. The signal 660 can be presumed for illustrative purposes to be the "preferred" sensing configuration at the outset. At times 662, 664, 666, and 668, signal 660 drops in signal quality. The repeated drops in signal quality can be treated as a trend in some examples, causing signal 660 to be ruled out entirely for future use, at least until physician intervention takes place to determine whether a failure, such as lead migration, lead fracture, or a problem with lead-canister coupling, for example, is occurring.

In the example of FIG. 12, signal 660 is not ruled out. Instead, at the first drop 662 in signal quality of the preferred signal 660, a vector switch is triggered as indicated by line 700. Upon return to higher signal quality for preferred signal 660, the sensing configuration reverts as indicated at 702. A minimum time period 704 is enforced, keeping the alternative sensing vector in place for a minimum period of time after the vector switch 700 occurs. This time period 704, in some examples, allows for the assurance that the signal quality of signal 660 has been assessed as "good" for a minimum duration after its original decline at 662.

At the second drop 664 in signal quality of the preferred signal 660, another vector switch is triggered, as indicated by line 710. However, this time, the minimum duration of the vector switch, shown at 714, has been extended. Such extension adds to the period of time that signal 660 must show high quality after the repeated drop in signal quality at 666, increasing the stability requirement before reversion. In one example, the extended duration may be fixed. In another example, the extended duration may be set in light of the time period between two most recent drops in signal quality. For example, the new minimum duration 714 may equal the default duration 704 plus the period between the two signal quality drops noted at 662 and 664.

Following the return to use of the preferred signal 660, another drop occurs at 666, generating a warning signal this time because the signal actually dropped below the lower sensing quality threshold for signal 660. This time, again, a sensing configuration change takes place as indicated by line 720. An even longer minimum duration 722 is enforced before return to the preferred sensing vector is enacted at 724. Duration 722 may be twice duration 714, for example or, as noted above, the new duration 722 may be set to be longer than the duration between observed signal quality declines at times 662, 664, 666 and/or 668, plus some minimum quantity. Once the preferred sensing vector stabilizes, as indicated at 670, for a relatively long period of time, the extended minimum durations may be decreased or reset, optionally.

The number of tiers to use for duration 702, 714, and 722 may be greater or less than those shown. In one example, duration 702 is chosen to allow settling of the circuitry and detection algorithm, using a minimum duration, for example, of one to sixty seconds. Duration 714 is chosen next to manage what could be deemed temporary issues such as the presence of large fields due to walking past a generator, or standing near a speaker briefly, and is in the range of one to ten minutes. Duration 722 may be chosen to anticipate unmanaged surgery (i.e, an MRI or electrocautery procedure where clinicians fail to turn a device off), a work situation or special circumstance such as a concert, and may be in the range of thirty minutes to twenty-four hours. Other general bases and ranges for selecting the durations may be selected. The time period for reducing the extended durations based on stability may be, for example, equal to or a multiple of the maximum such duration—for example, equal to or up to ten times, or more, the duration 722. The durations can also be a function of recently-observed patterns in the time-varying changes of signal quality.

Figure 13:
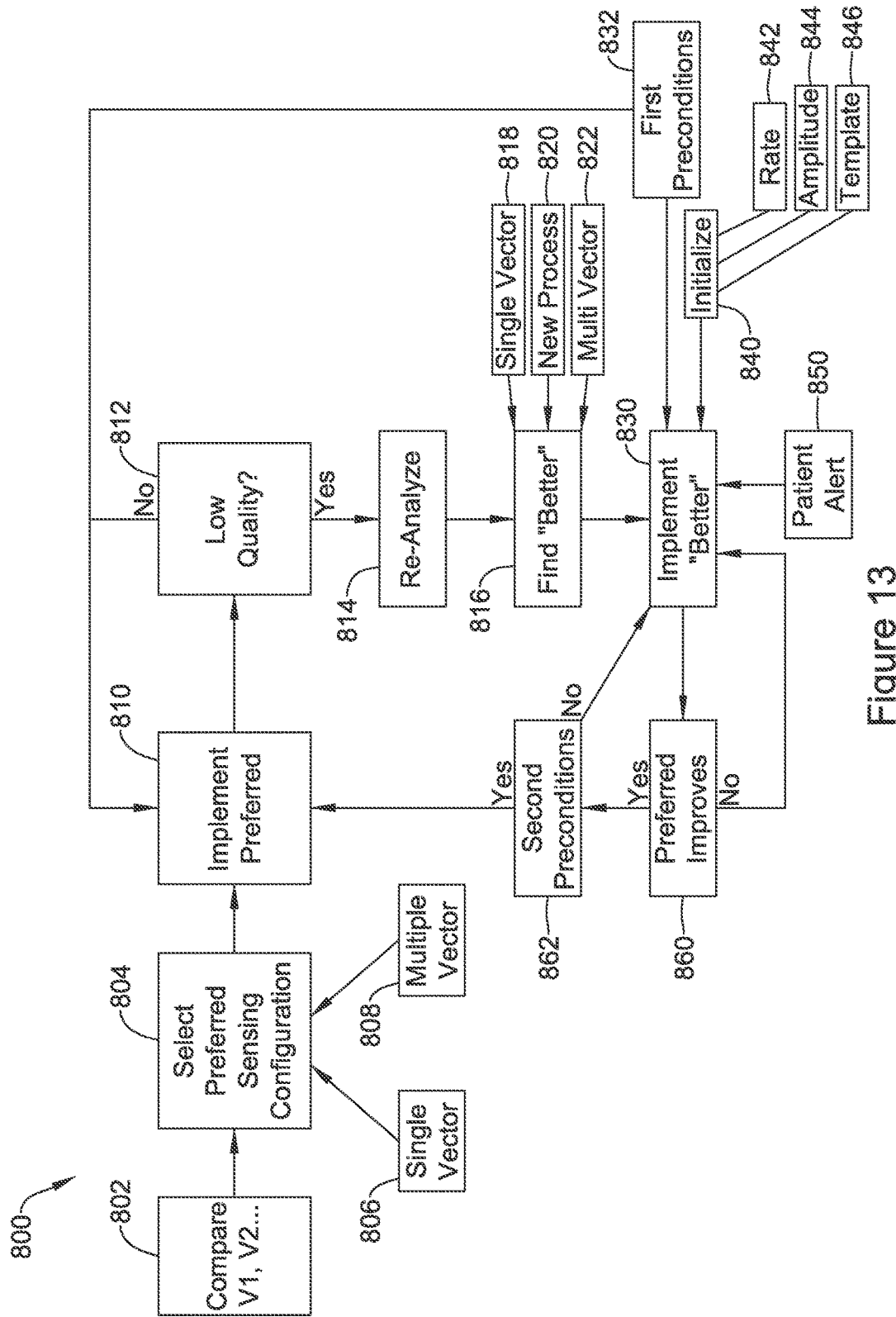
FIGS. 13-14 show illustrative methods in block flow form.
Figure 14:
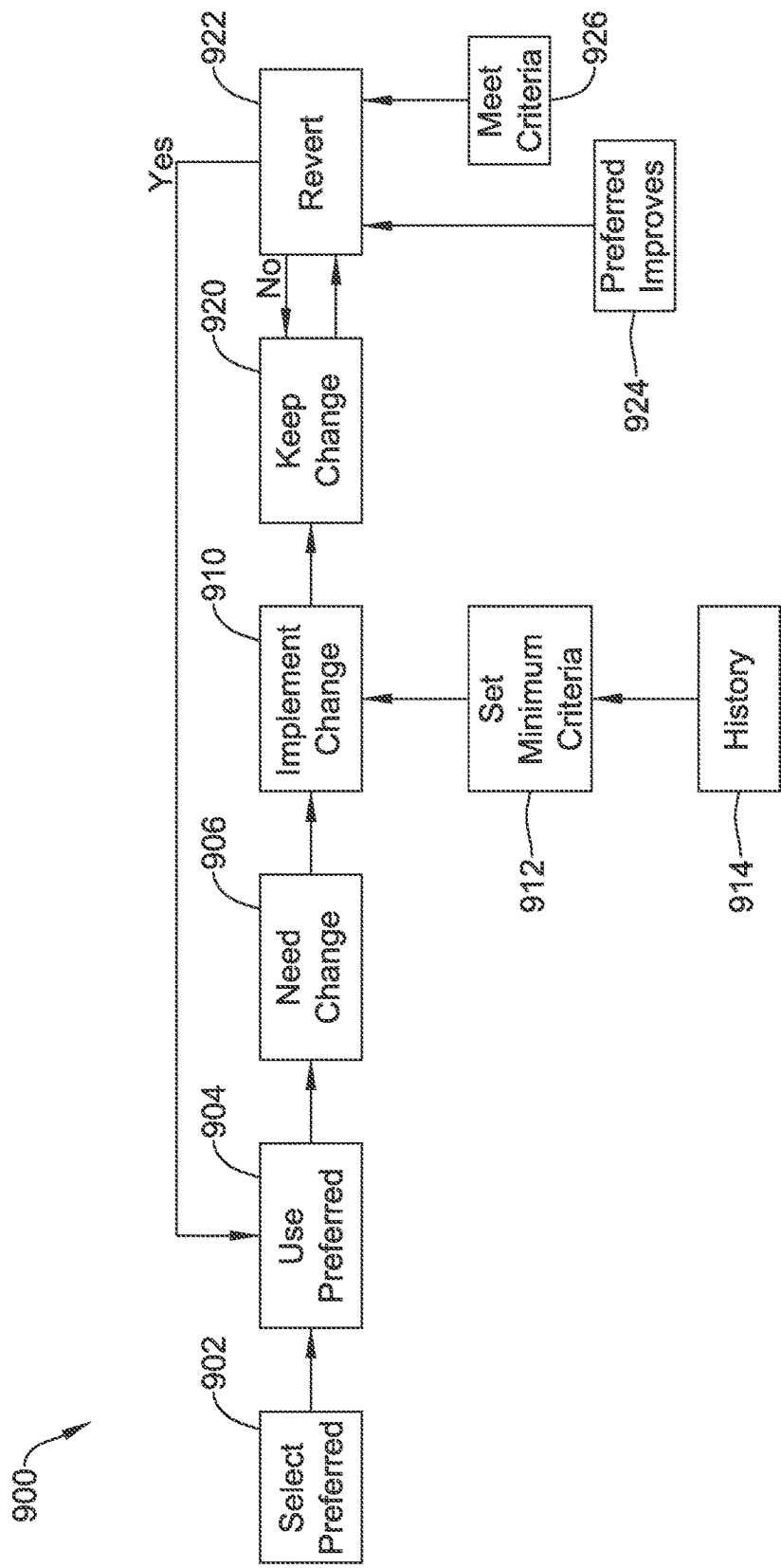

FIGS. 13-14 show illustrative methods in block flow form. Referring to FIG. 13, a method 800 begins by comparing a plurality of vectors V1, V2, etc. at 802 and selecting a preferred sensing configuration at 804. The preferred sensing configuration selected at 804 may be a single vector configuration, as indicated at 806, or a multiple vector configuration as indicated at 808, either by design or by nature of a selection of the "best" performing signal.

At 810 the preferred sensing vector configuration is implemented and used for cardiac signal analysis. Next, at 812, the preferred sensing vector configuration is analyzed to determine whether it is providing low quality signals. If not, the method simply returns to 810.

If low quality signals are found at 812, the method performs a re-analysis at 814 of the available sensing vectors and/or combinations thereof, in order to find a "Better" sensing vector configuration, as indicated at 816. From this point, in the diagram of FIG. 13, the word "Better" indicates the sensing vector configuration identified in block 816. The better configuration may be identified as a single sensing vector, as indicated at 818, which may be a different vector than originally selected, or may substitute a single vector for a multi-vector configuration. Alternatively, as indicated at 820, the better configuration may be identified using a new or different manner of processing the signal of single or plural vectors, for example, using different filtering parameters or, for a multi-vector configuration, selecting a different set of weighting factors to use with different sensing vectors. In still another example, a multi-vector configuration may be selected to replace a single vector configuration, as indicated at 822.

Next, the better sensing configuration is implemented as indicated at 830. The actual implementation of the better sensing configuration may be delayed until one or more first preconditions are met, as indicated at 832. For example, the first preconditions 832 may require that the patient not be in a high rate condition (not tachycardia or tachyarrhythmia, for example) or that the patient's posture or other physiological condition be stable, or that the patient not be active, as patient activity may create a low signal quality without necessitating sensing vector changes. Posture and/or activity level may be determined, for example, by including an accelerometer in a device to observe patient movement.

In one example, the first preconditions may simply pause at 830, waiting to be met before a selected new sensing vector configuration can be implemented. In another example, as shown, failure of the first preconditions may undo the assessment at 812/814/816, and return to the preferred implementation at 810. In the latter case, the first preconditions may instead be applied before the re-analysis takes place at 814, to save the computational efforts.

The implementation of the better sensing vector at 830 may also call for or await initialization indicated at 840. Initialization 840 may include storing, artificially, a rate 842 for the patient, or an amplitude estimate for cardiac signals 844, or establishing a template 846 with the better sensing configuration. For example, the seeding of rate 842 or amplitude 844 may be performed in a device where the use of a detection profile to define a time varying detection threshold for cardiac cycles self-adjusts in light of rate and/or amplitude. The methods and devices in U.S. Pat. No. 8,565,878, titled ACCURATE CARDIAC EVENT DETECTION IN AN IMPLANTABLE CARDIAC STIMULUS DEVICE, and U.S. Pat. No. 8,494,630, titled DATA MANIPULATION FOLLOWING DELIVERY OF A CARDIAC STIMULUS IN AN IMPLANTABLE CARDIAC STIMULUS DEVICE are illustrative.

In addition, a patient alert 850 may be issued prior to implementing the better sensing configuration at 830. For example, a patient alert may be an audible alert (a beeper, for example), a visible alert (flashing lights, for example), or tactile (a vibrator or buzzer), or combination thereof. A patient alert 850 may also be a communicated signal to a patient's cellphone, or to a clinical center, for example, where an operator may attempt to contact a given patient. The patient alert 850 may arise at other stages as well, including, for example, in association with a "Yes" outcome at block 812, for example similar to that described above with reference to blocks 372, 378 and/or 390 in FIG. 7.

Following implementation at 830, the performance of other sensing vectors is monitored including, in this example, checking for improved performance of the preferred sensing vector, as indicated at 860. If no improvement is observed, the better sensing configuration remains implemented, with the method returning to 830. If improvement meeting a threshold condition (one or more of exceeding an absolute threshold or exceeding performance of the better sensing configuration, for example) is observed at 860, a set of second preconditions may be assessed as indicated at 862. The second preconditions may include a minimum time duration, which may be extendible as shown above in FIG. 12, for implementation of the better sensing configuration, as well as the same preconditions noted at 832 such as finding the patient to be in a selected posture or having an activity level below a threshold. If the second preconditions are not met at 862, the method simply returns to 830 again. If the second preconditions are met at 862, the method returns to implement the preferred sensing configuration at 810.

Referring now to FIG. 14, in this example 900, a preferred sensing configuration is selected initially at 902, and then implemented at 904. A need for a change in sensing vectors is identified at 906. For example, a determination can be made that one or more of a drop in sensing signal quality, multiple or continuous noise detection, or excessive overdetection, is occurring, triggering a need for a change at 906. Some examples for block 906 are noted in U.S. Provisional Patent Application Ser. No. 62/245,757, titled SIGNAL QUALITY MONITORING FOR MULTIPLE SENSE VECTORS IN CARDIAC DEVICES, the disclosure of which is incorporated herein by reference.

A change is then implemented, as noted at 910. As part of implementing the change at 910, a set of minimum criteria 912 for the change may be set. Such minimum criteria 912 may include a requirement that the change remain in place for at least a minimum period of time, for example, or a minimum quantity of detected cardiac cycles. The minimum criteria 912 may be based, in part, on history of the device itself, and/or the preferred sensing configuration. For example, the time extensions discussed in relation to FIG. 12 may be accommodated by 912/914.

The change is then implemented at 920. The device determines whether to revert to the preferred sensing configuration at 922. The device may revert 922 upon finding that the preferred sensing configuration has improved as indicated at 924, and/or that the minimum criteria from 912 are met, as indicated at 926. In an alternative embodiment, the change at 906 may be triggered not by a finding of deterioration of the sensing quality of the preferred sense vector, but instead by improvement of the sensing signal quality of another sensing configuration. In this case, rather than block 924 calling for improvement of the preferred sensing configuration, instead, it may be a relative determination that the sensing configuration to which the device has changed is no longer superior to the original preferred sensing configuration.

Figure 15:
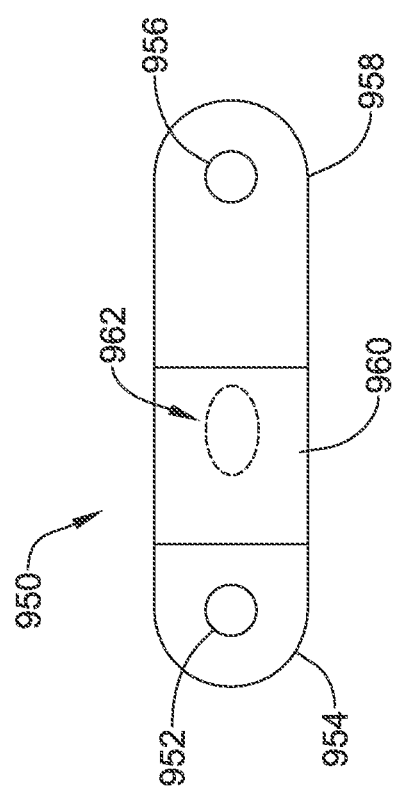
FIG. 15 shows an illustrative cardiac monitor.

FIG. 15 shows an implantable monitor. An implantable monitor may be implanted subcutaneously in most instances, though other positions such as intracardiac, epicardial, or below the ribs or behind/beneath the sternum may be used instead. The monitor 950 is shown as having a first sensing electrode 952 on a header 954 that may also include, for example, an antenna for communicating with an external or second internal device. A second sensing electrode is shown at 956 on the opposite end of the device 950 from the first electrode 952. The second sensing electrode may be provided on the outside of a battery 958, for example, which may or may not be rechargeable. Operational circuitry for this design may be provided in the central portion of the device, as indicated at 960. A third sensing electrode 962 is shown in phantom to indicate that it may be on the opposite side of the device from the first and second electrodes 952, 956. Other dispositions of the multiple electrodes may be used instead, such as those shown in U.S. Pat. No. 5,331,966, or those used in commercially available implantable cardiac monitors such as the various Medtronic Reveal™ products.

Figure 16:
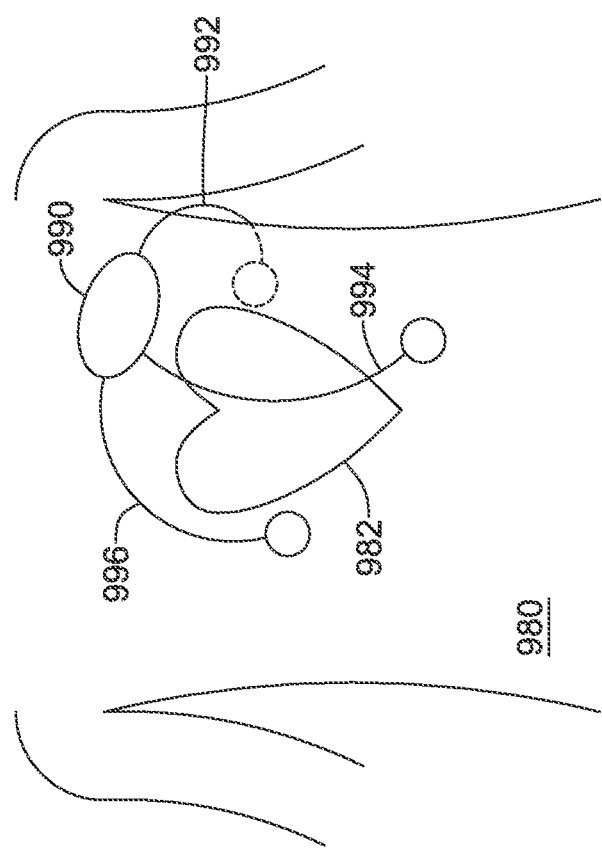
FIG. 16 shows an illustrative wearable cardiac device.

FIG. 16 illustrates a wearable cardiac rhythm management device. The system is shown on the torso 980 of a patient relative to the heart 982 of the patient. The external device may include, for example, a canister 990 having a power source and operational circuitry for the device, as well as a plurality of leads 992, 994, 996 connected to cutaneous electrodes on the front or back of the patient's torso 980. It is understood that the system may provide therapy or may be merely a monitor, and may take other forms. The system may be, for example, integrated in a wearable vest, or provided as an automated external defibrillator, or may be a smaller wearable product such as a Holter monitor or wearable patch, for example.

For the purposes of the present invention, the implantable therapy system (FIG. 1), implantable monitor (FIG. 15), or external device for therapy or monitoring (FIG. 16) may integrate the various improvements shown herein so long as there are multiple sensing configurations available. While most of the above discussion focuses on the availability of multiple sensing vectors, a sensing reconfiguration may instead call for changing one or more of sensing gain, sensing filtering, data rate, sampling rate, or other sensing features, in addition to or instead of simply considering a different sensing vector.

The blocks shown in FIGS. 6-10 and 13-14 may each be implemented as means to perform various analysis steps in several ways. For example, a means to calculate a new weighting factor for a given sensing vector may take the form of a block of software code for implementation/execution by a processor, controller, microprocessor or microcontroller. A means to calculate a new weighting factor for a given sensing vector may include or consist of dedicated hardware or an analog, digital or mixed signal application specific integrated circuit (ASIC). Likewise, other blocks in FIGS. 6-10 and 13-14 may be implemented as software and/or hardware.

Various examples above may be implemented in wearable or implantable devices. Such implementation may take place by including operational circuitry for receiving a signal from implantable electrodes, processing the signal and analyzing the processed signal to make decisions such as whether to store data or deliver therapy. Operational circuitry may be housed in a canister or canisters. The operational circuitry may include a controller (such as a microcontroller or microprocessor, or simply an application specific integrated chip (ASIC) such as an analog, mixed signal, or digital ASIC). The operational circuitry may instead or also include suitable analog and/or digital circuits needed for signal processing, memory storage and generation of high-power electrical, low-power electrical and/or non-electrical outputs. The operational circuitry may include suitable battery technology for an implantable device (rechargeable or primary cell), with any of numerous examples well known in the art, and may use various capacitor technologies to assist in the short term build-up and/or storage of energy for defibrillation or other output purposes.

The implantable or wearable components may be manufactured with biocompatible materials suitable for implantation or tissue contact, such as those widely known, along with coatings for such materials, throughout the art. For example, implantable devices can be made using titanium, with a titanium nitride or iridium oxide (or other material) coating if desired, and implantable leads can be formed with a biocompatible material such as a polyether, polyester, polyamide, polyurethane, polycarbonate, silicon rubber and blends or copolymers thereof. Alternatively, other biocompatible materials such as silver, gold, titanium, or stainless steel such as MP35N stainless steel alloy, or other materials may be used.

In some examples, the system may include one or more sensors to detect signals in addition to the cardiac electrical signal that can be captured using selected combinations of implantable or wearable electrodes. Such additional sensors may include, for example, temperature sensors, accelerometers, microphones, optical sensors and chemical sensors, among others. The programmer 22 and implantable device 12 may communicate with one another using, for example and without limitation, inductive or RF telemetry, or any other suitable communication solution. The present invention may be embodied in a system having any such characteristics.

A first non-limiting example takes the form of a cardiac rhythm management device having operational circuitry for analyzing cardiac signals including a least first and second cardiac sensing vectors and first and second sensing channels, wherein the operational circuitry is configured to use the at least first and second sensing vectors, the operational circuitry comprising: a first means for comparing one or more sensing quality metrics of the at least first and second cardiac sensing vectors (such as circuitry and or programming instructions represented in FIG. 7, block 352, for example); selector means for selecting one of the at least first and second cardiac sensing vectors as a preferred sensing configuration (such as circuitry and or programming instructions represented in FIG. 7, block 352, for example); implementer means for implementing the preferred sensing configuration to analyze cardiac signals (such as circuitry and or programming instructions represented in FIG. 7, block 362, for example); a first identifier means for identifying low sensing signal quality for the preferred sensing configuration (such as circuitry and or programming instructions represented in FIG. 7, block 370, for example); and analyzer means for re-analyzing sensing quality metrics of the at least first and second cardiac sensing vectors (such as circuitry and or programming instructions represented in FIG. 7, block 374, for example); a second identifier means for identifying a better sensing configuration than the preferred sensing configuration, at least as assessed at the time of the low sensing quality of the preferred sensing configuration (such as circuitry and or programming instructions represented in FIG. 7, block 376, for example); if one or more first preconditions are met, implementing the better sensing configuration to analyze cardiac signals (such as circuitry and or programming instructions represented in FIG. 7, block 380, for example); and monitor means for monitoring signal quality of the preferred sensing configuration until the low sensing quality for the preferred sensing configuration improves and one or more second preconditions are met, at which time the operational circuitry is configured to return to using the preferred sensing configuration (such as circuitry and or programming instructions represented in FIG. 7, block 360, for example).

A second non-limiting example takes the form of a cardiac rhythm management device as in the first non-limiting example wherein the preferred sensing configuration uses data from a single cardiac sensing vector, and the better sensing configuration uses data from plural cardiac sensing vectors.

A third non-limiting example takes the form of a cardiac rhythm management device as in the first non-limiting example wherein the preferred sensing configuration uses data from a single cardiac sensing vector, and the better sensing configuration uses data from a different cardiac sensing vector than the preferred sensing configuration.

A fourth non-limiting example takes the form of a cardiac rhythm management device as in the first non-limiting example wherein the preferred sensing configuration uses data from a single cardiac sensing vector, and the better sensing configuration uses data from either: the same cardiac sensing vector, but with a different application of one or more filtering or amplification characteristics than the preferred sensing configuration; or a different cardiac sensing vector than the preferred sensing configuration.

A fifth non-limiting example takes the form of a cardiac rhythm management device having operational circuitry for analyzing cardiac signals including a least first and second cardiac sensing vectors and first and second sensing channels, wherein the operational circuitry is configured to use the at least first and second sensing vectors, the operational circuitry comprising: a first means for comparing one or more sensing quality metrics of the at least first and second cardiac sensing vectors (such as circuitry and or programming instructions represented in FIG. 13, block 802, for example); selector means for selecting weighted sum of the at least first and second cardiac sensing vectors as a preferred sensing configuration (such as circuitry and or programming instructions represented in FIG. 13, block 804, for example); implementer means for implementing the preferred sensing configuration to analyze cardiac signals (such as circuitry and or programming instructions represented in FIG. 13, block 806, for example); a first identifier means for identifying low sensing signal quality for the preferred sensing configuration (such as circuitry and or programming instructions represented in FIG. 13, block 812, for example) and: analyzer means for re-analyzing sensing quality metrics of the at least first and second cardiac sensing vectors (such as circuitry and or programming instructions represented in FIG. 13, block 814, for example); a second identifier means for identifying a better sensing configuration than the preferred sensing configuration, at least as assessed at the time of the low sensing quality of the preferred sensing configuration (such as circuitry and or programming instructions represented in FIG. 13, block 816, for example); if one or more first preconditions are met, implementing the better sensing configuration to analyze cardiac signals (such as circuitry and or programming instructions represented in FIG. 13, blocks 830, 832, for example); and monitor means for monitoring signal quality of the preferred sensing configuration until the low sensing quality for the preferred sensing configuration improves and one or more second preconditions are met, at which time the operational circuitry is configured to return to using the preferred sensing configuration (such as circuitry and or programming instructions represented in FIG. 13, block 862, for example).

A sixth non-limiting example takes the form of a cardiac rhythm management device as in any of the first through fifth non-limiting examples wherein the first and second preconditions include a determination that no current tachyarrhythmia is ongoing.

A seventh non-limiting example takes the form of a cardiac rhythm management device as in any of the first through sixth non-limiting examples wherein the second preconditions include a determination that a minimum time period has expired since the better sensing configuration was implemented.

An eighth non-limiting example takes the form of a cardiac rhythm management device as in the seventh non-limiting example wherein the operational circuitry includes calculator means for calculating the minimum time period by reviewing history for the device, determining whether low sensing signal quality has been identified for the preferred sensing configuration repeatedly (such as circuitry and or programming instructions represented in FIG. 13, block 862 and FIG. 14, blocks 912, 914, for example) and selecting from: a first value longer than a second value if low sensing signal quality has been identified for the preferred sensing configuration repeatedly; or else the second value.

A ninth non-limiting example takes the form of a cardiac rhythm management device as in the seventh non-limiting example wherein the operational circuitry includes calculator means for calculating the minimum time period by reviewing history for the device, determining whether low sensing signal quality has been identified for the preferred sensing configuration repeatedly (such as circuitry and or programming instructions represented in FIG. 13, block 862 and FIG. 14, blocks 912, 914, for example) and selecting from: a first, default value; or a value which exceeds a time period between at least two instances of repeated drops in sensing signal quality.

A tenth non-limiting example takes the form of a cardiac rhythm management device as in any of the first to ninth non-limiting examples wherein the operational circuitry includes sensor means for sensing a posture of the patient and at least one of the preconditions comprises determining that the patient is remaining in a single posture (such as circuitry and or programming instructions represented in FIG. 13, blocks 832, 862, for example).

An eleventh non-limiting example takes the form of a cardiac rhythm management device as in any of the first to ninth non-limiting examples wherein the operational circuitry includes detector means for detecting an activity level of the patient and at least one of the preconditions comprises determining that the patient's activity level is below or above a threshold (such as circuitry and or programming instructions represented in FIG. 13, blocks 832, 862, for example).

A twelfth ninth non-limiting example takes the form of a cardiac rhythm management device having operational circuitry for analyzing cardiac signals including a least first and second cardiac sensing vectors and first and second sensing channels, wherein the operational circuitry is configured to use the at least first and second sensing vectors, the operational circuitry comprising: selector means for selecting a first sensing configuration as a preferred sensing configuration (such as circuitry and or programming instructions represented in FIG. 14, blocks 902, for example); identifier means for identifying low sensing signal quality for the preferred sensing configuration and identifying a better sensing configuration (such as circuitry and or programming instructions represented in FIG. 14, block 906, for example); implementer means for implementing the better sensing configuration until predetermined criteria are met (such as circuitry and or programming instructions represented in FIG. 14, block 910, for example); and upon meeting the predetermined criteria, reverting to use of the preferred sensing configuration (such as circuitry and or programming instructions represented in FIG. 14, blocks 922, 926, for example); wherein the predetermined criteria include at least two components: a first component calling for improved signal sensing quality in the preferred sensing configuration (such as circuitry and or programming instructions represented in FIG. 14, block 924, for example); and a second component referencing a history of the signal sensing quality in the preferred sensing configuration that increases a duration or likelihood of continued use of the better sensing configuration in response to repeated low sensing signal quality of the preferred sensing configuration (such as circuitry and or programming instructions represented in FIG. 14, block 914, for example).

A thirteenth non-limiting example takes the form of a cardiac rhythm management device as in the twelfth non-limiting example wherein the second component requires a minimum period of time expire, where in the minimum period of time is increased in response to repeated low sensing signal quality of the preferred sensing configuration.

A fourteenth non-limiting example takes the form of a cardiac rhythm management device as in the twelfth or thirteenth non-limiting examples wherein the second component references a history within a defined time window that is shorter than the life of the device.

A fifteenth non-limiting example takes the form of a cardiac rhythm management device as in any of the twelfth to fourteenth non-limiting examples wherein the predetermined criteria includes a third component comparing the sensing signal quality of the preferred sensing configuration to the sensing signal quality of the better sensing configuration.

A sixteenth non-limiting example takes the form of a cardiac rhythm management device as in any of the first to fifteenth non-limiting examples wherein the operational circuitry includes initializer means for initializing the better sensing configuration before the better sensing configuration is implemented (such as circuitry and or programming instructions represented in FIG. 13, block 840, for example).

A seventeenth non-limiting example takes the form of a cardiac rhythm management device as in the sixteenth non-limiting example wherein: the initializer means for initializing initializes the better sensing configuration at least by seeding a value for cardiac cycle rate from memory, without reference to a signal detected using the better sensing configuration; and the operational circuitry includes means for using a detection profile for analyzing cardiac signals by applying a time varying detection threshold to cardiac signals to detect cardiac cycles, the time varying detection threshold being defined by the detection profile, wherein the detection profile changes in accordance with cardiac cycle rate, such that seeding a value for cardiac cycle rate affects the detection profile of the better sensing configuration (such as circuitry and or programming instructions represented in FIG. 13, blocks 840, 842, for example).

An eighteenth non-limiting example takes the form of a cardiac rhythm management device as in the sixteenth non-limiting example wherein: the initializer means for initializing initializes the better sensing configuration at least by determining a cardiac rate using an autocorrelation analysis and storing the cardiac rate; and the operational circuitry includes means for using a detection profile for analyzing cardiac signals by applying a time varying detection threshold to cardiac signals to detect cardiac cycles, the time varying detection threshold being defined by the detection profile, wherein the detection profile changes in accordance with cardiac rate, such that storing a cardiac rate affects the detection profile of the better sensing configuration (such as circuitry and or programming instructions represented in FIG. 13, blocks 840, 842, for example).

A nineteenth non-limiting example takes the form of a cardiac rhythm management device as in any of the sixteenth to eighteenth non-limiting examples wherein: the initializer means for initializing initializes the better sensing configuration at least by seeding a value for cardiac cycle amplitude from memory, without reference to a signal detected using the better sensing configuration; and the operational circuitry includes means for using a detection profile for analyzing cardiac signals by applying a time varying detection threshold to cardiac signals to detect cardiac cycles, the time varying detection threshold being defined by the detection profile and an estimate of cardiac cycle amplitude, such that seeding a value for cardiac cycle amplitude affects the detection profile of the better sensing configuration (such as circuitry and or programming instructions represented in FIG. 13, blocks 840, 844, for example).

A twentieth non-limiting example takes the form of a cardiac rhythm management device as in any of the sixteenth to eighteenth non-limiting examples wherein the initializer means for initializing initializes the better sensing configuration at least by forming a template of normal cardiac cycle activity for the better sensing configuration (such as circuitry and or programming instructions represented in FIG. 13, blocks 840, 846, for example).

A twenty-first non-limiting example takes the form of a cardiac rhythm management device having operational circuitry for analyzing cardiac signals including a least first and second cardiac sensing vectors, wherein the operational circuitry is configured to use the at least first and second sensing vectors, the operational circuitry comprising: selector means for selecting a first sensing configuration as a preferred sensing configuration, the first sensing configuration using data from only one of the at least first and second cardiac sensing vectors, and implementing the first sensing configuration to analyze cardiac signals (such as circuitry and or programming instructions represented in FIG. 10, block 550, for example); identifier means for identifying low sensing signal quality for the first sensing configuration (such as circuitry and or programming instructions represented in FIG. 10, block 554, for example); and analyzer means for analyzing a plurality of individual sensing vectors and determining whether any have sensing signal quality that at least exceeds the sensing signal quality of the first sensing configuration and a signal quality threshold (such as circuitry and or programming instructions represented in FIG. 10, block 560, for example), and: a) if so, the identifier means identifying a second sensing configuration to replace, at least temporarily, the preferred sensing configuration, the second sensing configuration using data from only one of the at least first and second cardiac sensing vectors, and implementing the second sensing configuration to analyze cardiac signals (such as circuitry and or programming instructions represented in FIG. 10, blocks 570, 572, for example); or b) if not, the identifier means identifying a third sensing configuration to replace, at least temporarily, the preferred sensing configuration, the third sensing configuration combining data from at least two of the at least first and second cardiac sensing vectors, and implementing the third sensing configuration to analyze cardiac signals (such as circuitry and or programming instructions represented in FIG. 10, blocks 570, 580, for example).

A twenty-second non-limiting example takes the form of a cardiac rhythm management device as in the twenty-first non-limiting example wherein the operational circuitry includes means for reverting to the first sensing configuration in the event that the sensing signal quality for the first sensing configuration improves (such as circuitry and or programming instructions represented in FIG. 10, blocks 576, 552, for example).

A twenty-third non-limiting example takes the form of a cardiac rhythm management device as in any of the first to twenty-second non-limiting examples wherein the operational circuitry includes means for providing an alert to the patient regarding change of the sensing vectors before implementing the better sensing configuration (such as circuitry and or programming instructions represented in FIG. 13, block 850, for example).

A twenty-fourth non-limiting example takes the form of a cardiac rhythm management device as in any of the first to twenty-third non-limiting examples wherein the cardiac rhythm management devices comprises an implantable defibrillator, cardiac resynchronization device, pacemaker, or cardiac monitor.

A twenty-fifth non-limiting example takes the form of a cardiac rhythm management device as in any of the first to twenty-third non-limiting examples wherein the cardiac rhythm management devices comprises an external and/or wearable defibrillator, pacemaker, or cardiac monitor.

A twenty-sixth non-limiting example takes the form of operating a cardiac rhythm management device as in any of the first to twenty-fifth non-limiting examples for the monitoring of cardiac rhythms in a patient.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A cardiac rhythm management device having operational circuitry for analyzing cardiac signals including a least first and second cardiac sensing vectors and first and second sensing channels, wherein the operational circuitry is configured to use the at least first and second sensing vectors as follows:
   comparing one or more sensing quality metrics of the at least first and second cardiac sensing vectors;
   selecting one of the at least first and second cardiac sensing vectors as a preferred sensing configuration based on the comparison of the one or more sensing quality metrics;
   implementing the preferred sensing configuration to analyze cardiac signals, detect cardiac cycles, and calculate cardiac rate;
   identifying low sensing signal quality for the preferred sensing configuration and:
   re-analyzing sensing quality metrics of the at least first and second cardiac sensing vectors;
   identifying a better sensing configuration than the preferred sensing configuration based on the re-analysis of the sensing quality metrics, at least as assessed at the time of the low sensing quality of the preferred sensing configuration;
   if one or more first preconditions are met, implementing the better sensing configuration to analyze cardiac signals, wherein the operational circuitry is configured to initialize the better sensing configuration before the better sensing configuration is implemented; and
   monitoring signal quality of the preferred sensing configuration until the low sensing quality for the preferred sensing configuration improves and one or more second preconditions are met, at which time the operational circuitry is configured to return to using the preferred sensing configuration: wherein:
   the operational circuitry is configured to initialize the better sensing configuration at least by seeding a value for cardiac cycle amplitude from memory of the device, without reference to a signal detected using the better sensing configuration; and
   the operational circuitry is configured to detect cardiac cycles using a detection profile defining a time varying detection threshold by applying the time varying detection threshold to cardiac signals and detecting a new cardiac cycle when the time varying detection threshold is crossed by the cardiac signal, the time varying detection threshold being defined in part by an estimate of cardiac cycle amplitude, such that seeding a value for cardiac cycle amplitude affects the detection threshold.

2. The device of claim 1 wherein the operational circuitry is adapted to detect cardiac cycles by:
   analyzing data from a single cardiac sensing vector while using the preferred sensing configuration, and
   analyzing data from a plurality of cardiac sensing vectors while using the better sensing configuration.

3. The device of claim 1 wherein the operational circuitry is adapted to detect cardiac cycles by:
analyzing data from a first single cardiac sensing vector while using the preferred sensing configuration, and
analyzing data from a second single cardiac sensing vector different from the first single cardiac sensing vector while using the better sensing configuration.

4. The device of claim 1 wherein the operational circuitry is configured such that the preferred sensing configuration uses data from a single cardiac sensing vector for detecting cardiac cycles, and the better sensing configuration uses data from either:
the same cardiac sensing vector, but with a different application of one or more filtering or amplification characteristics than the preferred sensing configuration; or
a different cardiac sensing vector than the preferred sensing configuration,
for detecting cardiac cycles.

5. The device of claim 1 wherein the operational circuitry is configured to sense a posture of the patient and at least one of the preconditions comprises determining that the patient is remaining in a single posture.

6. The device of claim 1 wherein the operational circuitry is configured to detect an activity level of the patient and at least one of the preconditions comprises determining that the patient's activity level is below or above a threshold.

7. The device of claim 1 wherein initialization of the better sensing configuration includes at least forming a template of normal cardiac cycle activity for the better sensing configuration.

8. The device of claim 1 wherein the operational circuitry is configured to provide an alert to the patient regarding change of the sensing vectors before implementing the better sensing configuration.

9. The device of claim 1 wherein the operational circuitry is configured to calculate one or more sensing quality metrics by observing peak amplitude of a sensed cardiac signal.

10. A cardiac rhythm management device having operational circuitry for analyzing cardiac signals including a least first and second cardiac sensing vectors and first and second sensing channels, wherein the operational circuitry is configured to use the at least first and second sensing vectors as follows:
comparing one or more sensing quality metrics of the at least first and second cardiac sensing vectors;
selecting one of the at least first and second cardiac sensing vectors as a preferred sensing configuration based on the comparison of the one or more sensing quality metrics;
implementing the preferred sensing configuration to analyze cardiac signals, detect cardiac cycles, and calculate cardiac rate;
identifying low sensing signal quality for the preferred sensing configuration and:
re-analyzing sensing quality metrics of the at least first and second cardiac sensing vectors;
identifying a better sensing configuration than the preferred sensing configuration based on the re-analysis of the sensing quality metrics, at least as assessed at the time of the low sensing quality of the preferred sensing configuration;
if one or more first preconditions are met, implementing the better sensing configuration to analyze cardiac signals, wherein the operational circuitry is configured to initialize the better sensing configuration before the better sensing configuration is implemented; and
monitoring signal quality of the preferred sensing configuration until the low sensing quality for the preferred sensing configuration improves and one or more second preconditions are met, at which time the operational circuitry is configured to return to using the preferred sensing configuration;
further comprising a non-transitory device memory, wherein:
the operational circuitry is configured to initialize the better sensing configuration at least by seeding a value for cardiac cycle rate from the device memory, without reference to a signal detected using the better sensing configuration; and
the operational circuitry is configured to detect cardiac cycles using a detection profile defining a time varying detection threshold by applying the time varying detection threshold to cardiac signals and detecting a new cardiac cycle when the time varying detection threshold is crossed by the cardiac signal, wherein the time varying detection threshold of the detection profile changes in accordance with cardiac cycle rate, such that seeding a value for cardiac cycle rate affects the detection threshold.

11. A cardiac rhythm management device having operational circuitry for analyzing cardiac signals including a least first and second cardiac sensing vectors and first and second sensing channels, wherein the operational circuitry is configured to use the at least first and second sensing vectors as follows:
comparing one or more sensing quality metrics of the at least first and second cardiac sensing vectors;
selecting one of the at least first and second cardiac sensing vectors as a preferred sensing configuration based on the comparison of the one or more sensing quality metrics;
implementing the preferred sensing configuration to analyze cardiac signals, detect cardiac cycles, and calculate cardiac rate;
identifying low sensing signal quality for the preferred sensing configuration and:
re-analyzing sensing quality metrics of the at least first and second cardiac sensing vectors;
identifying a better sensing configuration than the preferred sensing configuration based on the re-analysis of the sensing quality metrics, at least as assessed at the time of the low sensing quality of the preferred sensing configuration;
if one or more first preconditions are met, implementing the better sensing configuration to analyze cardiac signals, wherein the operational circuitry is configured to initialize the better sensing configuration before the better sensing configuration is implemented; and
monitoring signal quality of the preferred sensing configuration until the low sensing quality for the preferred sensing configuration improves and one or more second preconditions are met, at which time the operational circuitry is configured to return to using the preferred sensing configuration; wherein:
the operational circuitry is configured to initialize the better sensing configuration at least by determining a cardiac rate using an autocorrelation analysis and storing the cardiac rate; and the operational circuitry is configured to detect cardiac cycles using a detection profile defining a time varying detection threshold by applying the time varying detection threshold to cardiac signals and detecting a new cardiac cycle when the time varying detection threshold is crossed by the cardiac signal, wherein the time varying detection threshold of the detection profile changes in accordance with cardiac rate, such that storing a cardiac rate affects the detection threshold.

* * * * *